United States Patent
Schultz

(10) Patent No.: US 8,002,757 B1
(45) Date of Patent: Aug. 23, 2011

(54) SPLASH SHIELD SYSTEMS

(76) Inventor: Joseph P. Schultz, Atlanta, GA (US)

( * ) Notice: Subject to any disclaimer, the term of this patent is extended or adjusted under 35 U.S.C. 154(b) by 993 days.

(21) Appl. No.: 11/753,560

(22) Filed: May 24, 2007

Related U.S. Application Data

(63) Continuation-in-part of application No. 11/317,758, filed on Dec. 23, 2005, now Pat. No. 7,311,695, which is a continuation-in-part of application No. 10/245,241, filed on Sep. 17, 2002, now abandoned, which is a continuation-in-part of application No. 10/123,966, filed on Apr. 16, 2002, now Pat. No. 7,802,574, which is a continuation of application No. 09/484,666, filed on Jan. 18, 2000, now abandoned.

(60) Provisional application No. 60/803,109, filed on May 24, 2006.

(51) Int. Cl.
*A61M 35/00* (2006.01)
*A61M 31/00* (2006.01)

(52) U.S. Cl. ........ 604/289; 604/296; 604/310; 604/311; 604/268

(58) Field of Classification Search .................. 604/289, 604/300, 290, 296, 311–313, 263, 192, 35, 604/36, 315–316, 23, 310, 268; 433/80, 433/96, 116
See application file for complete search history.

(56) References Cited

U.S. PATENT DOCUMENTS

| | | |
|---|---|---|
| 3,648,696 A | 3/1972 | Keith |
| D295,380 S | 4/1988 | Virag et al. |
| 4,769,003 A | 9/1988 | Stamler |
| 4,898,588 A | 2/1990 | Roberts |
| 5,030,214 A | 7/1991 | Spector |
| 5,078,694 A | 1/1992 | Wallace |
| D344,133 S | 2/1994 | Stamler |
| D345,016 S | 3/1994 | Stamler |
| 5,735,833 A | 4/1998 | Olson |
| 5,795,324 A | 8/1998 | Morse |
| 5,830,197 A * | 11/1998 | Rucinski ............ 604/290 |
| 5,941,859 A | 8/1999 | Lerman |
| 6,093,182 A | 7/2000 | Lampropoulis et al. |
| 6,210,381 B1 | 4/2001 | Morse |
| 6,293,929 B1 | 9/2001 | Smith et al. |
| 6,402,724 B1 | 6/2002 | Smith et al. |

OTHER PUBLICATIONS

Judd Hollander, Wound Registry: Development and Validation, article, May 1995, Annals of Emergency Medicine.
Richard Edlich, Wound Irrigation, editorial, Jul. 1994, Annals of Emergency Medicine.
John Howell, Outpatient Wound Preparation and Care: A National Survey, article, Aug. 1992, Annals of Emergency Medicine.
Adam Singer, Pressure Dynamics of Various Irrigation Techniques Commonly Used in the Emergency Department, article, Jul. 1994, Annals of Emergency Medicine.
Judd Hollander, Irrigation of Facial and Scalp Lacerations: Does It Alter Outcome?, article, Jan. 1998, Annals of Emergency Medicine.
Thomas Stephenson, Cleansing the Traumatic Wound by High Pressure Syringe Irrigation, article, Jan. 1976, JACEP, vol. 5, No. 1. Carey Chisolm, Comparison of a New Pressurized Saline Cannister Versus Syringe Irrigation for Laceration Cleansing in the Emergency Department, article, Nov. 1992, Annals of Emergency Medicine.
Richard Edlich, Principles of Emergency Room Management, article, Dec. 1988, Annals of Emergency Medicine.
Jeffrey Morse, Wound Infection Rate and Irrigation Pressure of Two Potential New Wound Irrigation Devices: The Port and the Cap, article, Jan. 1988, American Journal of Emergency Medicine, vol. 16, No. 1.

* cited by examiner

*Primary Examiner* — Jacqueline F Stephens
(74) *Attorney, Agent, or Firm* — Stoneman Law Patent Group; Martin L. Stoneman

(57) ABSTRACT

Splash shield systems for use with wide mouth irrigation squeeze bottles and other irrigation fluid sources.

69 Claims, 16 Drawing Sheets

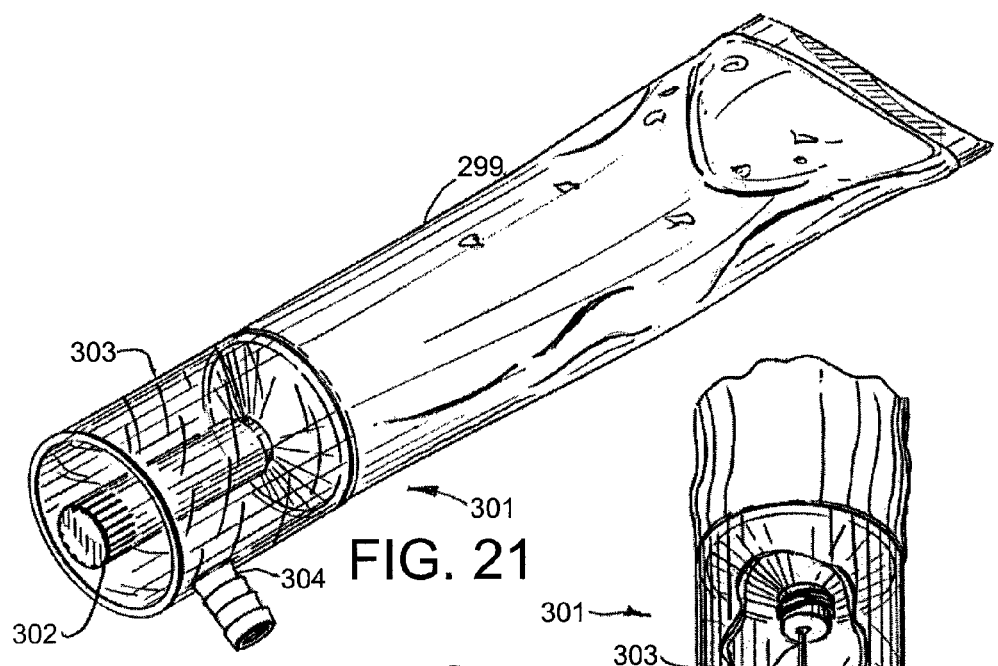
FIG. 21
FIG. 22
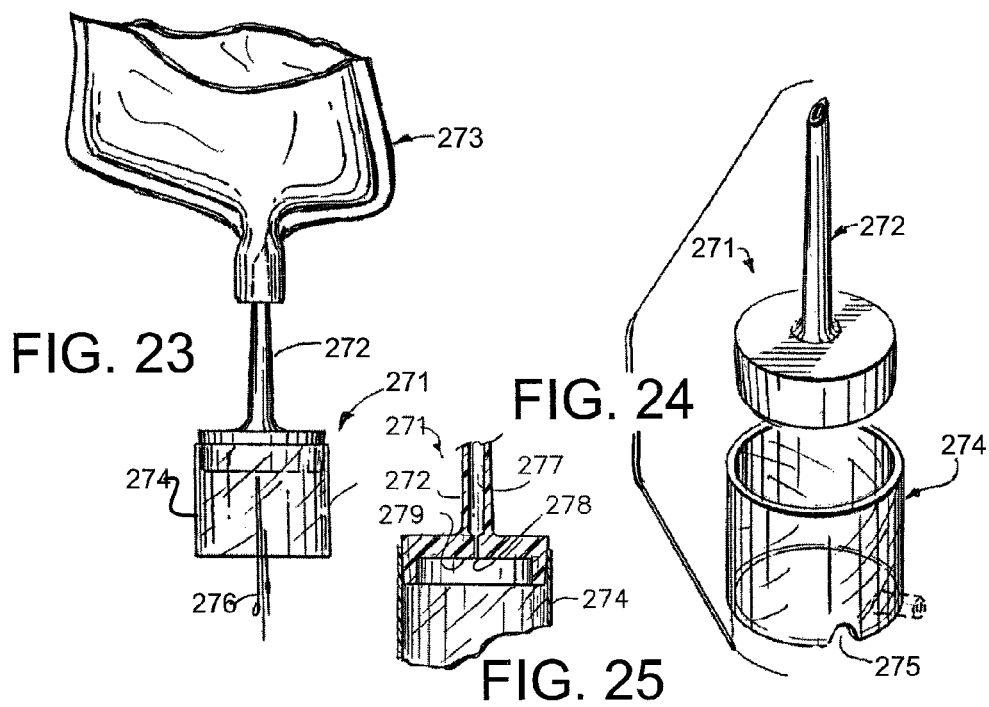
FIG. 23
FIG. 24
FIG. 25

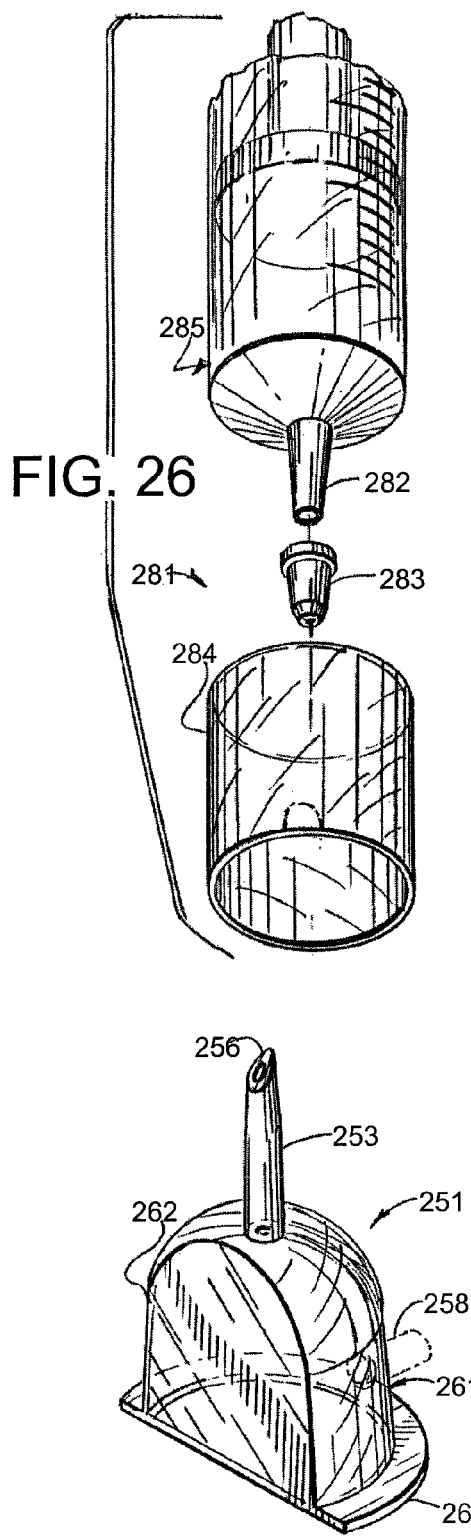
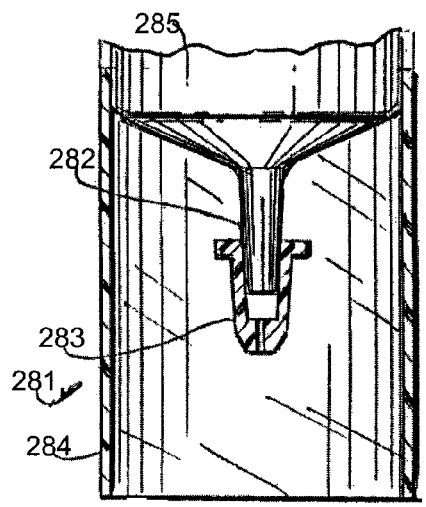
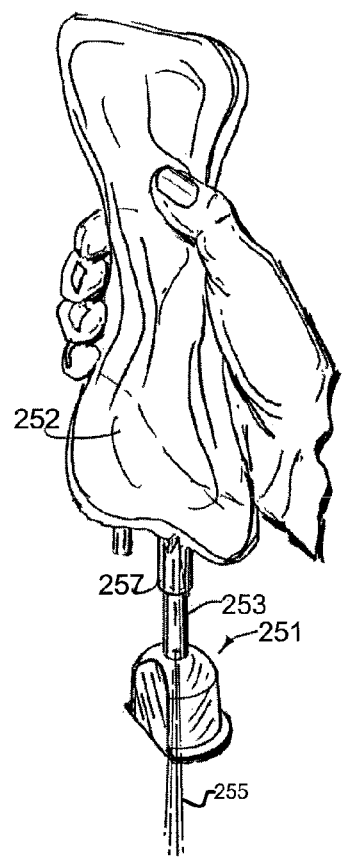
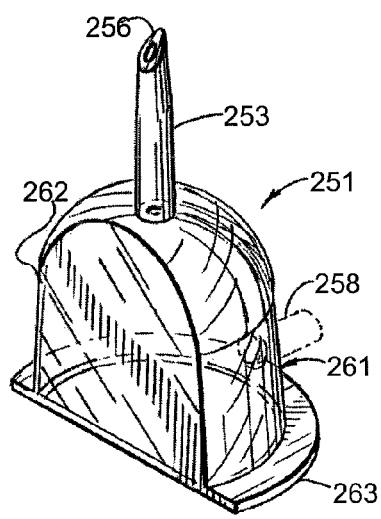
FIG. 26
FIG. 27
FIG. 29
FIG. 28

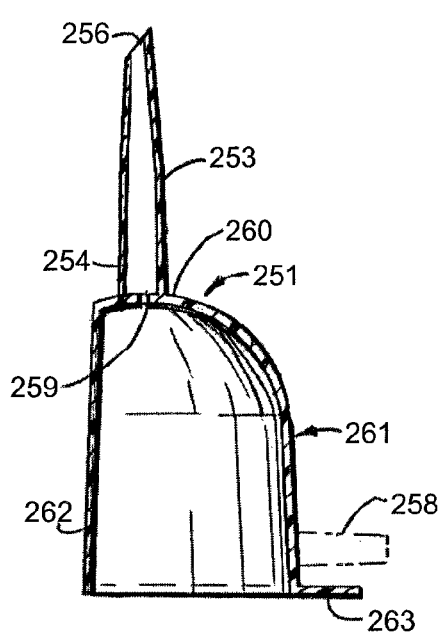
FIG. 30
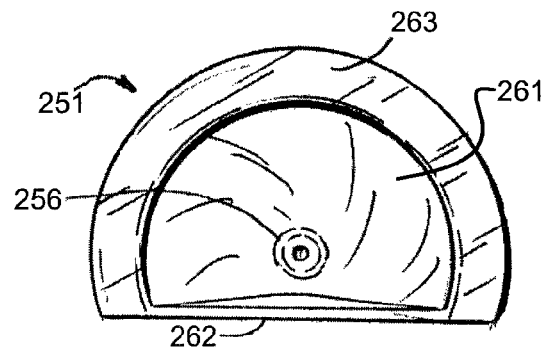
FIG. 31
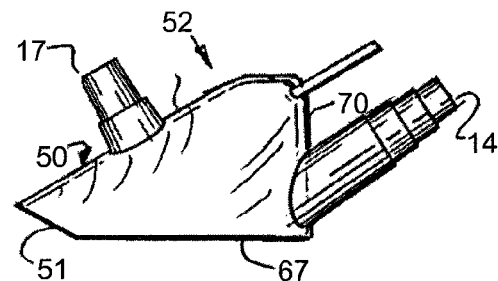
FIG. 32
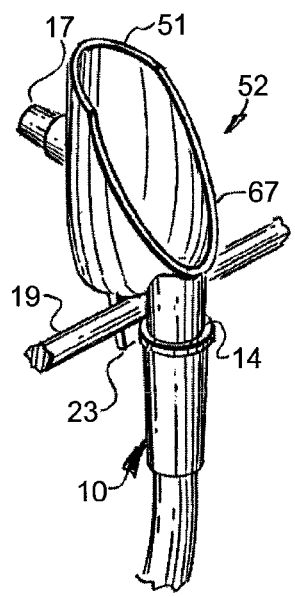
FIG. 34
FIG. 33
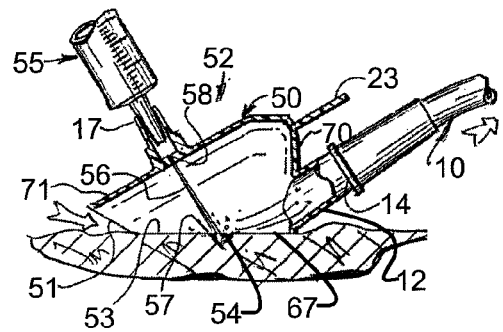
FIG. 35

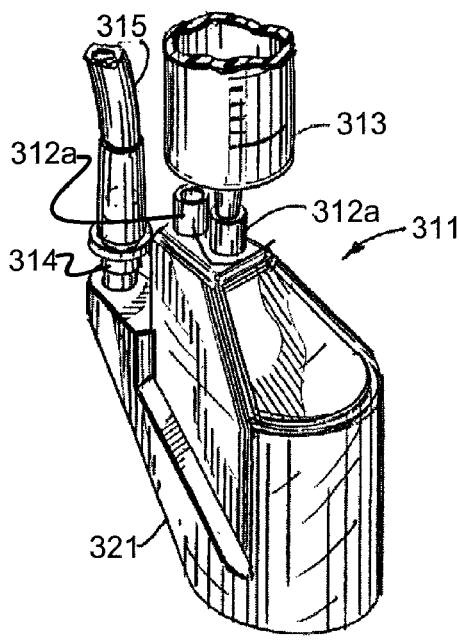
FIG. 41
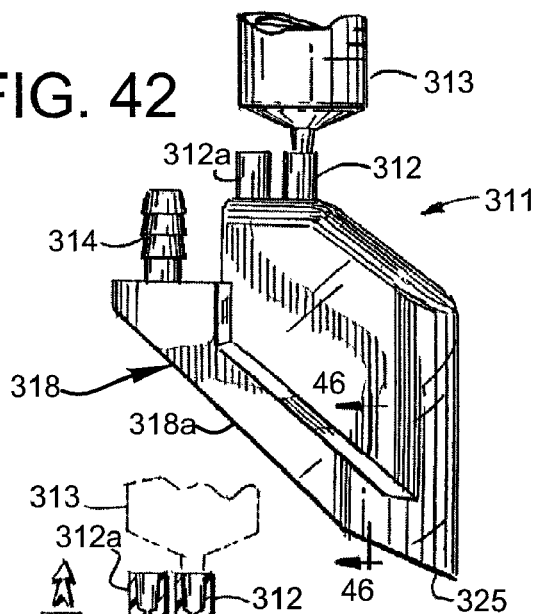
FIG. 42
FIG. 43
FIG. 44
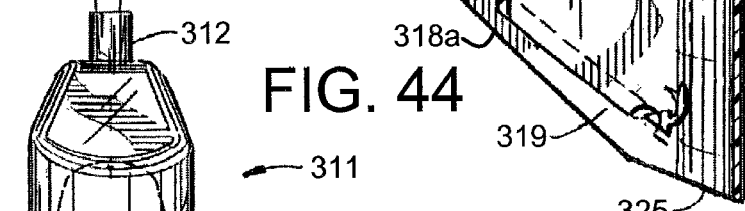
FIG. 46
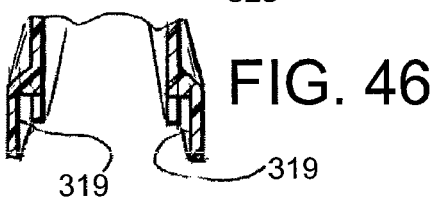
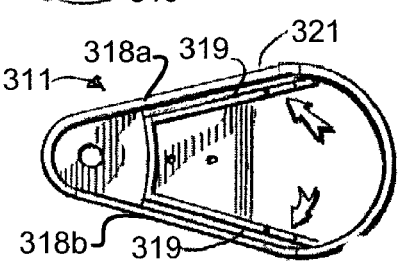
FIG. 45
FIG. 47

SPLASH SHIELD SYSTEMS

CROSS-REFERENCE TO RELATED APPLICATIONS

The present application is a continuation-in-part of related U.S. utility patent application Ser. No. 11/317,758, filed Dec. 23, 2005, entitled "SPLASH SHIELD SYSTEM", which is a continuation-in-part of U.S. utility patent application Ser. No. 10/245,241, filed Sep. 17, 2002, entitled "SPLASH SHIELD SYSTEM", which is a continuation-in-part of U.S. utility patent application Ser. No. 10/123,966, filed Apr. 16, 2002, entitled "MEDICAL COMPONENT SYSTEM", which is a continuation-in-part of related U.S. utility patent application Ser. No. 09/484,666, filed Jan. 18, 2000, entitled "MEDICAL COMPONENT SYSTEM", and is related to and claims priority from prior provisional application Ser. No. 60/803,109, filed May 24, 2006, entitled "SPLASH SHIELD SYSTEM", all of which are incorporated herein by this reference, and which are not admitted to be prior art with respect to the present invention by the mention in this cross-reference section.

BACKGROUND OF THE INVENTION

This invention relates to providing a medical system assisting more efficient and safer performance of medical procedures. More particularly, this invention concerns a medical system comprising apparatus and methods for improved irrigation and lavage. With respect to irrigation problems, when a patient has a wound, it is desirable to irrigate the wound with a solution such as normal saline. Presumably the dilution effect of the irrigation will wash out bacteria and debris and prevent wound contamination, infection, and scarring. The more fluid, the greater the degree of success in prevention. A higher pressure of irrigation could also help remove bacteria and push out unwanted debris. Unfortunately, when using large volumes or high amounts of pressures, there is a high likelihood of contaminated fluid spreading to unwanted surfaces, including splashing onto a health care provider or drenching the patient. This is undesirable as the risk of spreading of disease is heightened and there are undesirable effects of getting a patient wet (for example, a trauma patient with multiple wounds might be hypothermic from a large amount of irrigation fluid evaporating on his body, or a child with a facial laceration might become hypothermic from the excess fluid wetting its clothing during the winter). The excess fluid will also soil laundry and require increased housekeeping services, using existing methods of irrigation. This is also an inconvenience for otherwise healthy patients. They may have to remove their clothing to prevent them from getting soaked. This may be uncomfortable for the patient in a busy emergency room; and the time necessary for the patient to disrobe would delay a doctor's or nurse's ability to treat such patient or other waiting patients more expeditiously. These disadvantages will decrease the incentive for an operator, such as a physician, to appropriately use optimal large volumes of irrigation fluid; and therefore the risk of wound complications will increase. Still another disadvantage, in addition to the small diameter discharge port of a prior art syringe shield, is that when an operator empties a syringe using a prior art syringe shield, the operator must actively detach the shield from the syringe to refill the syringe to apply a large volume of fluid to a wound because of the small volume capacity of syringes. This active step is one more that will discourage a user who, for example, is in a busy emergency room, from using the optimal large volume of irrigation fluid.

OBJECTS AND FEATURES OF THE INVENTION

A primary object and feature of the present invention is to fulfill the above-mentioned needs by the provision of an improved splash shield system. A further primary object and feature of this invention is to provide a splash shield system which provides a horizontal vector to the forces of the irrigation fluid on the wound. Another primary object and feature of this invention is to provide a splash shield system which easily accommodates connection to a variety of different sources of irrigation fluid. Another primary object and feature of the present invention is to provide such a splash shield system which is efficient, inexpensive, and handy. Another primary object and feature of the present invention is to provide such a splash shield system which can be easily manipulated by the user to direct the irrigation fluid to different locations. Other objects and features of this invention will become apparent with reference to the following specification and claims.

SUMMARY OF THE INVENTION AND ADVANTAGES

In accordance with a preferred embodiment hereof, this invention provides a splash shield system, related to protecting at least one user of at least one squeezable wide mouth irrigation fluid bottle from contact with irrigation fluid from at least one squeezable wide mouth irrigation fluid bottle directed at a patient's wound, such splash shield system comprising: at least one body comprising at least one first end and at least one second end; at least one squeezable wide mouth irrigation fluid bottle connector structured and arranged to connect such at least one body, at such at least one first end, to the at least one squeezable wide mouth irrigation fluid bottle; wherein such at least one body comprises at least one inner hollow; and at least one irrigation fluid port; wherein such at least one second end is open to such at least one inner hollow forming at least one shield structured and arranged to protect against contact with irrigation fluid; and wherein such at least one irrigation fluid port permits fluid communication between such at least one first end and such at least one inner hollow. Moreover, it provides such a splash shield system wherein such at least one squeezable wide mouth irrigation fluid bottle connector comprises internal threads structured and arranged to provide threaded connection with external threads on at least one bottle neck finish of the at least one squeezable wide mouth irrigation fluid bottle. Additionally, it provides such a splash shield system wherein such threads have standard thread dimensions. Also, it provides such a splash shield system wherein such standard thread dimensions comprise a 1½-6 UNC thread dimension. In addition, it provides such a splash shield system wherein such standard thread dimensions comprise a 1½-6 UNC coarse thread dimension. And, it provides such a splash shield system wherein such threads comprise at least 2.5 turns. Further, it provides such a splash shield system wherein such threads comprise helical threads with at least 2 turns. Even further, it provides such a splash shield system wherein such at least one body comprises at least one substantially cylindrical wall portion. Moreover, it provides such a splash shield system wherein such at least one substantially cylindrical wall portion is substantially round. Additionally, it provides such a splash shield system wherein such at least one shield is substantially cylindrical. Also, it provides such a splash shield system wherein such at least one shield is substantially round. In addition, it provides such a splash shield system wherein such at least one substantially round shield comprises at least one side port structured and arranged to permit evacuation of irrigation fluid temporarily contained by such at least one inner hollow. And, it provides such a splash shield system wherein such at least one squeezable wide mouth irrigation fluid bottle connector is structured and arranged to connect to at least one standard wide mouth irrigation fluid pour bottle. Further, it provides such a splash shield system wherein such at least one squeezable wide mouth irrigation fluid bottle connector is structured and arranged to connect to standard wide mouth irrigation fluid pour bottles from multiple manufacturers. Even further, it provides such a splash shield system wherein such at least one squeezable wide mouth irrigation fluid bottle connector is structured and arranged to connect to standard wide mouth irrigation fluid pour bottles from at least three manufacturers. Moreover, it provides such a splash shield system wherein such at least one squeezable wide mouth irrigation fluid bottle connector is structured and arranged to connect to multiple bottle finish types. Additionally, it provides such a splash shield system wherein such at least fluid irrigation port comprises at least one large area. Also, it provides such a splash shield system wherein such at least one large area comprises an area greater than a port having at least about 1.5 mm diameter. In addition, it provides such a splash shield system wherein such at least one squeezable wide mouth irrigation fluid bottle connector is structured and arranged to connect to at least one squeezable wide mouth irrigation fluid bottle neck finish portion comprising at least one outer diameter between about 4/5 inches and about 1 3/4 inches. And, it provides such a splash shield system wherein such at least one squeezable wide mouth irrigation fluid bottle connector is structured and arranged to connect to at least one squeezable wide mouth irrigation fluid bottle having a volume between about 250 cubic centimeters and about 1750 cubic centimeters. Further, it provides such a splash shield system wherein such at least one squeezable wide mouth irrigation fluid bottle connector comprises at least one inner diameter between about 4/5 inches and about 1 3/4 inches. Even further, it provides such a splash shield system wherein such at least one squeezable wide mouth irrigation fluid bottle connector comprises at least one inner diameter between about 1.3 inches and about 1.6 inches. Moreover, it provides such a splash shield system wherein such at least one inner hollow is capable of temporarily containing at least one volume of irrigation fluid, such at least one volume of irrigation fluid being greater than about 25 milliliters, when such at least one shield is adjacent a body surface of the patient during irrigation. Additionally, it provides such a splash shield system further comprising at least one partition separating such at least one first end from such at least one second end; wherein such at least one irrigation fluid port comprises at least one nozzle; and wherein such at least one partition comprises such at least one nozzle, protruding from such at least one partition, structured and arranged to direct at least one stream of irrigation fluid from the at least one squeezable wide mouth irrigation fluid bottle when the at least one squeezable wide mouth irrigation fluid bottle is squeezed. Also, it provides such a splash shield system wherein such at least one nozzle comprises at least one inlet port; at least one passageway; and at least one outlet port; wherein such at least one passageway comprises at least one cross-sectional area; and wherein such at least one cross-sectional area decreases from such at least one inlet port of such at least one nozzle to such at least one outlet port of such at least one nozzle. In addition, it provides such a splash shield system wherein such at least one nozzle protrudes from such at least one partition a distance between about 0.005 inches to about 1 inch. And, it provides such a splash shield system wherein such at least one nozzle comprises at least one passageway comprising at least one passageway length between about 0.005 inches to about 1 inch. Further, it provides such a splash shield system wherein such at least one shield is substantially transparent to permit viewing irrigation of the patient's wound when irrigation fluid is applied to the patient's wound. Even further, it provides such a splash shield system wherein such at least one squeezable wide mouth irrigation fluid bottle connector comprises at least one washer structured and arranged to form a seal when such at least one squeezable wide mouth irrigation fluid bottle connector is connected to the at least one squeezable wide mouth irrigation fluid bottle. Moreover, it provides such a splash shield system wherein such at least one body consists of one monolithic piece. Additionally, it provides such a splash shield system wherein such at least one irrigation fluid port comprises at least two holes structured and arranged to dispense irrigation fluid towards the patient's wound. Also, it provides such a splash shield system wherein such at least one body is sterile. In addition, it provides such a splash shield system wherein such at least one shield comprises at least one side port structured and arranged to permit evacuation of irrigation fluid temporarily contained by such at least one inner hollow.

In accordance with another preferred embodiment hereof, this invention provides a splash shield system, related to protecting at least one user of at least one squeezable wide mouth irrigation fluid bottle from contact with irrigation fluid from at least one squeezable wide mouth irrigation fluid bottle directed at a patient's wound, such splash shield system comprising: at least one body comprising at least one first end and at least one second end; at least one squeezable wide mouth irrigation fluid bottle; at least one wide mouth irrigation fluid bottle connector structured and arranged to connect such at least one body, at such at least one first end, to such at least one squeezable wide mouth irrigation fluid bottle; wherein such at least one body comprises at least one first inner hollow and at least one second inner hollow; and at least one fluid outlet; wherein such at least one fluid outlet is positioned between such at least one first inner hollow and such at least one second inner hollow; wherein such at least one second end is open to such at least one first inner hollow forming at least one shield structured and arranged to protect against contact with irrigation fluid; wherein such squeezable wide mouth irrigation fluid bottle connector comprises internal threads structured and arranged to provide threaded connection with external threads on at least one bottle neck finish of the at least one squeezable wide mouth irrigation fluid bottle; and wherein such at least one shield is transparent to permit viewing irrigation of the patient's wound when irrigation fluid is applied to the patient's wound. And, it provides such a splash shield system wherein such at least one first inner hollow is capable of temporarily containing at least one volume of irrigation fluid, such at least one volume of irrigation fluid being greater than about 25 milliliters, when the at least one shield is adjacent a body surface of the patient during irrigation. Further, it provides such a splash shield system wherein such at least one squeezable wide mouth irrigation fluid bottle connector is structured and arranged to connect to at least one standard wide mouth irrigation fluid pour bottle. Even further, it provides such a splash shield system wherein such at least one squeezable wide mouth irrigation fluid bottle connector is structured and arranged to connect to standard wide mouth irrigation fluid pour bottles from at least three manufacturers. Even further, it provides such a splash shield system wherein such at least one squeezable wide mouth irrigation fluid bottle connector is structured and arranged to connect to multiple bottle finish types. Even further, it provides such a splash shield system wherein such at least fluid irrigation port comprises at least one large area. Even further, it provides such a splash shield system wherein such at least one large area comprises an area greater than a port having at least about 1.5 mm diameter. Even further, it provides such a splash shield system wherein such at least one body is sterile.

In accordance with a preferred embodiment hereof, this invention provides a splash shield system for irrigation of a patient's wound and suction removal of excess irrigation fluid, comprising: a body structured and arranged to contain irrigation fluid, wherein such body has a maximum height dimension, and an input opening structured and arranged to allow the irrigation fluid into such body, wherein such input opening is located at a substantially lower position than such maximum height dimension. Moreover, it provides such a splash shield system further comprising: an output opening structured and arranged to allow suctioning excess irrigation fluid from within such body; wherein such output opening is structured and arranged to draw excess irrigation fluid from such body toward a location approximately at a position symmetrically opposed (with respect to such maximum height dimension) from the location of such input opening. Additionally, it provides such a splash shield system wherein: a bottom peripheral circumference of such body has an oval-like shape. Also, it provides such a splash shield system wherein such input opening comprises: a swivel structured and arranged to allow a user to direct a stream of irrigation fluid to selected portions of the skin of a patient; wherein such swivel comprises an attacher structured and arranged to allow attachment of a source of irrigation fluid to such swivel. In addition, it provides such a splash shield system wherein such output opening further comprises: an output nozzle structured and arranged to attach to a vacuum line; a conduit structured and arranged to direct suction flow across such splash portion toward such output nozzle; wherein such conduit comprises at least one channel along a periphery of such body extending from such output nozzle to a location approximately at a position symmetrically opposed from the location of such input opening. And, it provides such a splash shield system further comprising an irrigation-source connector structured and arranged to connect such input opening to a source of irrigation fluid; wherein such irrigation-source connector is structured and arranged to allow a luer connection. Further, it provides such a splash shield system wherein such input opening is structured and arranged to assist in directing irrigation fluid at an oblique angle from vertical.

Additionally, in accordance with a preferred embodiment hereof, this invention provides a splash shield system for protecting a user from contact with irrigation fluid directed at a patient's wound comprising: a body; having a first end and a second end, and a cylindrical exterior wall an irrigation-source connector structured and arranged to connect such body, at such first end, to a source of irrigation fluid; wherein such body comprises at least one inner hollow; wherein such second end, is open to such at least one inner hollow; wherein such splash shield system is structured and arranged in such manner as to protect the user from contact with the irrigation fluid. Even further, it provides such a splash shield system wherein such cylindrical exterior wall is substantially round; and such at least one inner hollow comprises a substantially round cylinder. Moreover, it provides such a splash shield system further comprising a source of irrigation fluid connected to such body at a such first end of such body. Additionally, it provides such a splash shield system further comprising an adapter structured and arranged to allow a connection between such body and such source of irrigation fluid. Also, it provides such a splash shield system wherein such adapter allows connection of such body to multiple varieties of such source of irrigation fluid. In addition, it provides such a splash shield system wherein such adapter comprises a nozzle structured and arranged to direct a stream of the irrigation fluid towards the wound. And, it provides such a splash shield system wherein such adapter comprises threads structured and arranged to provide a threaded connection with the source of irrigation fluid. Further, it provides such a splash shield system wherein such threads comprise internal threads structured and arranged to connect with external threads on a neck of a irrigation fluid bottle. Even further, it provides such a splash shield system further comprising: a bottle structured and arranged to contain irrigation fluid, such bottle comprising, a neck, wherein such neck comprises external threads structured and arranged to connect with a bottle cap. Moreover, it provides such a splash shield system further comprising: at least one end cap wherein such at least one end cap comprises a cap portion structured and arranged to close at least one end of such body. Additionally, it provides such a splash shield system wherein such at least one end cap covers and seals at least one end of such body in such manner as to protect internal sterility of such body. Also, it provides such a splash shield system wherein at least one such end cap portion of a such end cap comprises an externally-open pocket extending into such hollow cylindrical portion of such end cap. In addition, it provides such a splash shield system wherein such adapter comprises an IV-spike connector.

Further, in accordance with a preferred embodiment hereof, this invention provides a splash shield system for protecting a user from contact with irrigation fluid directed at a patient's wound comprising: a body, having a first end and a second end wherein such first end is open to a first hollow portion of such body and such second end is open to a second hollow portion of such body; an irrigation-source connector structured and arranged to connect such body, adjacent the first end, to a source of irrigation fluid; a partition, between such first hollow portion and such second hollow portion, (at least about the area of an irrigation bottle-neck); wherein such partition comprises at least one nozzle structured and arranged to direct at least one stream of the irrigation fluid towards the wound; wherein such splash shield system is structured and arranged in such manner as to protect the user from contact with the irrigation fluid. And, it provides such a splash shield system wherein such partition further comprises, at least one hole through such partition (in addition to such nozzle). Further, it provides such a splash shield system wherein such irrigation-source connector comprises threads structured and arranged to provide a threaded connection. Even further, it provides such a splash shield system wherein such threads comprise helical threads. Moreover, it provides such a splash shield system wherein such irrigation-source connector further comprises at least one adapter structured and arranged to provide a connection to a syringe tip.

Also, in accordance with a preferred embodiment hereof, this invention provides a splash shield system for protecting a user from contact with irrigation fluid directed at a patient's wound comprising: a body structured and arranged to assist in protecting a user from contact with irrigation fluid directed at a patient's wound; an irrigation-source connector structured and arranged to connect such body, at a first end of such body, to a source of irrigation fluid; wherein such irrigation-source connector comprises a puncturer structured and arranged to puncture at least one barrier between such body and the source of irrigation fluid. Additionally, it provides such a splash shield system wherein such puncturer comprises a spike. Also, it provides such a splash shield system wherein such spike comprises at least one opening structured and arranged to transport the irrigation fluid from the source of irrigation fluid to such body. In addition, it provides such a splash shield system wherein such spike comprises an IV-spike connector, unitary with such body.

Additionally, in accordance with a preferred embodiment hereof, this invention provides a splash shield system for protecting a user from contact with irrigation fluid directed at a patient's wound comprising: a transparent body structured and arranged to assist in protecting a user from contact with irrigation fluid directed at a patient's wound; an irrigation-source connector structured and arranged to connect such body, at a first end of such body, to a source of irrigation fluid; wherein such transparent body comprises at least one bottom opening wherein a bottom periphery of such at least one bottom opening is substantially non-planar. Also, it provides such a splash shield system wherein such bottom peripheral circumference is structured and arranged to allow rocking such body. And, it provides such a splash shield system wherein such bottom peripheral circumference is saddle-shaped.

Additionally, in accordance with a preferred embodiment hereof, this invention provides a splash shield system comprising: a transparent body structured and arranged to assist in protecting a user from contact with irrigation fluid directed at a patient's wound; an irrigation-source connector structured and arranged to connect such body to a source of irrigation fluid; wherein such body includes at least one bottom opening; wherein the ratio of a maximum length of such at least one bottom opening compared to a maximum width of such at least one bottom opening is at least 1.5:1.0.

In accordance with a preferred embodiment hereof, this invention provides a splash shield system, related to protecting a user from contact with irrigation fluid directed at a patient's wound, comprising: at least one body, comprising at least one first end and at least one second end; wherein such at least one first end comprises at least one irrigation-source connector; wherein such at least one second end comprises at least one inner hollow; wherein such at least one first end is in fluid communication with such at least one second end via at least one fluid discharge port; wherein such at least one inner hollow is structured and arranged to assist in containing fluid discharged from such at least one fluid discharge port; wherein such at least one fluid discharge port has a diameter of at least 1.5 mm. Moreover, it provides such a splash shield system wherein such at least one irrigation-source connector comprises threads structured and arranged to provide a threaded connection with threads on at least one finish of at least one wide mouth wound irrigation squeeze bottle. Additionally, it provides such a splash shield system wherein such at least one discharge port has a diameter of at least 2 mm. Also, it provides such a splash shield system wherein such at least one discharge port has a diameter of at least 2.5 mm.

In accordance with another preferred embodiment hereof, this invention provides a splash shield system, related to protecting a user from contact with irrigation fluid directed at a patient's wound, comprising: at least one body, comprising at least one first end and at least one second end; wherein such at least one first end comprises at least one irrigation-source connector; wherein such at least one second end comprises at least one inner hollow; wherein such at least one first end is in fluid communication with such at least one second end via at least one fluid discharge port; wherein such at least one inner hollow is structured and arranged to assist in containing fluid discharged from such at least one fluid discharge port; wherein such at least one irrigation-source connector comprises threads structured and arranged to provide a threaded connection with threads on at least one bottle finish of at least one wide mouth wound irrigation squeeze bottle; wherein such at least one irrigation-source connector is structured and arranged to accommodate a range of sizes of such at least one bottle finish to provide a liquid-tight seal. In addition, it provides such a splash shield system wherein such at least one irrigation-source connector comprises at least one surface structured and arranged to seal against the inner diameter of such at least one bottle finish. And, it provides such a splash shield system wherein such at least one irrigation-source connector comprises at least one washer; and such at least one washer comprises resilient material. Further, it provides such a splash shield system wherein such at least one irrigation-source connector comprises resilient material. Even further, it provides such a splash shield system wherein such at least one irrigation-source connector is structured and arranged to accommodate a range of sizes of such at least one standard irrigation bottle finish to provide a liquid-tight seal. Moreover, it provides such a Splash shield system wherein such at least one irrigation-source connector is structured and arranged to provide a liquid-tight seal that prevents leakage when irrigation pressures of 4 psi are generated through the at least one fluid discharge port. Additionally, it provides such a Splash shield system wherein such at least one irrigation-source connector is structured and arranged to provide a liquid-tight seal that prevents leakage when irrigation pressures of 7 psi are generated through the at least one fluid discharge port. Also, it provides such a Splash Shield system wherein such at least one surface comprises at least one circular ridge with at least one ridge outer surface which comprises at least one external taper. In addition, it provides such a splash shield system wherein such at least one circular ridge comprises at least one ridge outer surface diameter of less than 1.14 inches. And, it provides such a splash shield system wherein such at least one circular ridge comprises at least one ridge outer surface diameter greater than 1.2 inches. Further, it provides such a splash shield system wherein such at least one circular ridge comprises a range of ridge outer surface diameters, including ridge outer surface diameters from 1.14 inches to 1.2 inches. Even further, it provides such a Splash Shield system wherein such at least one irrigation-source connector is structured and arranged to accommodate a range of sizes of such at least three standard irrigation bottles with at least three different inner diameters bottle to provide a liquid-tight seal. Moreover, it provides such a Splash Shield system wherein such at least one irrigation-source connector is structured and arranged to provide a liquid-tight seal which universally fits standard irrigation bottles manufactured by BAXTER, ABBOT, and MCGAW. Additionally, it provides such a Splash Shield system wherein such at least one irrigation-source connector is structured and arranged to provide a liquid-tight seal which universally fits standard irrigation bottles with bottle finish inner diameters of about 1.14 inches, about 1.17 inches, and about 1.20 inches. Also, it provides such a Splash shield system wherein the liquid-tight seal prevents leakage where irrigation pressures of 4 psi are generated through the at least one fluid discharge port. In addition, it provides such a Splash shield system wherein the liquid-tight seal prevents leakage where irrigation pressures of 7 psi are generated through the at least one fluid discharge port. And, it provides such a splash shield system wherein such at least one inner hollow comprises at least one transparent portion.

In accordance with another preferred embodiment hereof, this invention provides a splash shield system, related to protecting a user from contact with irrigation fluid directed at a patient's wound, comprising: at least one body, comprising at least one first end and at least one second end; wherein such at least one first end comprises at least one irrigation-source connector; wherein such at least one second end comprises at least one inner hollow; wherein such at least one first end is in fluid communication with such at least one second end via at least one fluid discharge port; wherein such at least one inner hollow is structured and arranged to assist in containing fluid discharged from such at least one fluid discharge port; wherein such at least one irrigation-source connector comprises threads structured and arranged to provide a threaded connection with threads on at least one bottle finish of at least one standard wide mouth wound irrigation squeeze bottle; wherein such irrigation source connector threads have standard thread dimension. Further, it provides such a splash shield system wherein such standard thread dimension comprises a 1½-6 UNC thread dimension. Even further, it provides such a splash shield system wherein such standard thread dimension comprises a 1½-6 UNC coarse thread dimension. Even further, it provides such a splash shield system wherein such threads comprise helical threads with at least 2 turns. Even further, it provides such a splash shield system wherein such threads comprise at least 2.5 turns. Even further, it provides such a Splash shield system wherein such at least one inner hollow comprises at least one transparent portion. Even further, it provides such a Splash shield system wherein such at least one fluid discharge port comprises a plurality of fluid discharge ports.

BRIEF DESCRIPTION OF DRAWINGS

FIG. 21 is a perspective view of a preferred embodiment of a combined splash shield and irrigation squeeze tube according to the present invention.

FIG. 22 is a partial perspective view of the embodiment of FIG. 21, partially cut away to show its use with cap removed.

FIG. 23 is front view illustrating yet another preferred embodiment of a splash shield according to the present invention, showing a spike connector attached to a squeeze bag and also fitted into a cylindrical splash shield element.

FIG. 24 is a perspective view of the embodiment of FIG. 23, showing the spike connector separated from the cylindrical splash shield element.

FIG. 25 is a partial sectional view showing the connection details with the spike connector attached to the cylindrical splash shield element.

FIG. 26 is an exploded perspective view of yet another preferred embodiment of the splash shield of the present invention, showing a syringe-type end, a syringe adapter to control the irrigation stream, and a tubular splash shield element.

FIG. 27 is a sectional view of the embodiment of FIG. 26 illustrating the details with the parts connected.

FIG. 28 is a perspective view of yet another preferred embodiment of a splash shield according to the present invention shown attached to an IV-type squeeze bag by way of the IV spike connector of this embodiment.

FIG. 29 is an enlarged (over FIG. 28) perspective view of the embodiment of FIG. 28.

FIG. 30 is sectional side view of the embodiment of FIG. 28 illustrating the structural details thereof.

FIG. 31 is a bottom view of the embodiment of FIG. 28.

FIG. 32 is a side elevation view of a preferred embodiment of the splash shield medical device of the present invention.

FIG. 33 is a top plan view of the embodiment of FIG. 32.

FIG. 34 is a perspective view of the embodiment of FIG. 32 showing it in a restrained position.

FIG. 35 is a side sectional view of the embodiment of FIG. 32, illustrating its operation.

FIG. 41 is a perspective view of yet another preferred embodiment of a splash shield according to the present invention, shown with an inlet attached to an irrigation syringe and an outlet attached to a vacuum line.

FIG. 42 is a side view of the embodiment of FIG. 41, shown attached to the irrigation syringe.

FIG. 43 is a front view of the embodiment of FIG. 41, with the irrigation syringe in dotted lines.

FIG. 44 is a side sectional view of the embodiment of FIG. 41 showing the structural details and fluid flow directions FIG. 45 is a top view of the embodiment of FIG. 41.

FIG. 46 is a partial sectional view through the section 46-46 of FIG. 42.

FIG. 47 is a bottom view of the embodiment of FIG. 41.

DETAILED DESCRIPTION OF THE BEST MODES AND PREFERRED EMBODIMENTS OF THE INVENTION

Figure 1:
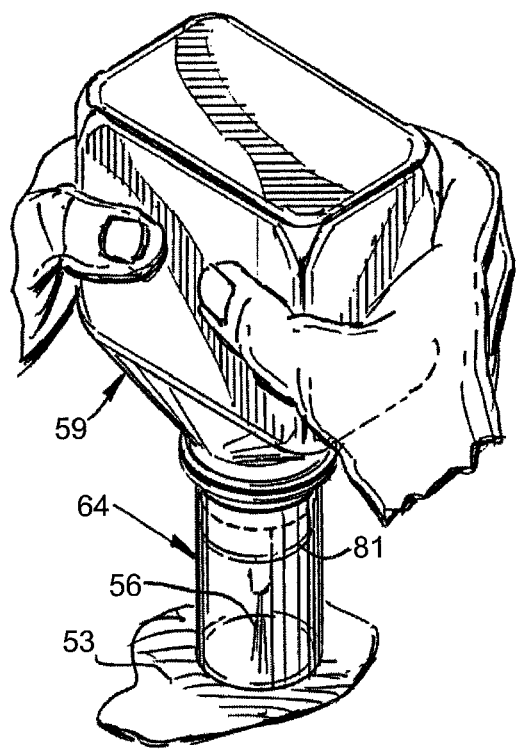
FIG. 1 is a perspective view of a preferred embodiment of a splash shield system according to the present invention, and showing use with an irrigation squeeze bottle.

FIG. 1 is a perspective view of a preferred embodiment of a splash shield system according to the present invention, showing use of splash shield 64 attached to wide mouth irrigation squeeze bottle 59. Preferably, wide mouth irrigation squeeze bottle 59 comprises a standard high volume plastic squeeze bottle of sterile fluid (sometimes also referred to herein as irrigation fluid), as shown. Preferably, wide mouth irrigation squeeze bottle 59 comprises a volume of at least about 250 cc. Preferably, wide mouth irrigation squeeze bottle 59 comprises a volume less than about 1750 cc. Preferably, wide mouth irrigation squeeze bottle 59 comprises bottle neck finish portion 30, as shown. Preferably, bottle neck finish portion 30 comprises an inner diameter between about ¾ inches and about 1½ inches, most preferably between about ⅘ inches and about 1¼ inches. Preferably, bottle neck finish portion 30 comprises an outer diameter between about ⅘ inches and about 1¾ inches. Preferably, wide mouth irrigation squeeze bottle 59 comprises a standard wide mouth wound irrigation squeeze bottle, such as, for example, wide mouth wound irrigation squeeze bottles manufactured and/or distributed by Baxter Healthcare Corporation (or Baxter International, Inc.) of Deerfield, Il. (sometimes referred to herein as BAXTER), Abbott Laboratories of Abbott Park, Il. (and related company Hospira Worldwide, Inc., of Lake Forest, Il.) (sometimes referred to herein as ABBOTT), or B. Braun Medical, Inc. of Allentown, Pa. (and related company McGaw, Inc., of Irvine, Ca.) (sometimes referred to herein as MCGAW). Preferably, when wide mouth irrigation squeeze bottle 59 is squeezed, fluid 56 is squirted onto flesh 53 (also referred to herein as body surface) of the patient, as shown. It is preferred that a wide mouth irrigation fluid bottle is used to reduce time filling up a basin or bath by pouring the contents of the irrigation fluid bottle into such basin or bath and then filling up a syringe from such basin or bath. Even if a syringe that has dimensions that may allow a user to insert the syringe into a wide mouth bottle is used, the syringe volume capacity is such that it will be time consuming and cumbersome to fill and refill the syringe to adequately irrigate the wound. Syringe shields cannot be inserted into a wide mouth bottle. To use a syringe shield with a wide mouth irrigation fluid bottle, a user must disconnect and reconnect the shield to the syringe each time the user needs to refill the syringe with irrigation fluid. Again, this is time consuming, cumbersome, and inefficient. Using the splash cap system of the present invention overcomes these problems.

Figure 2:
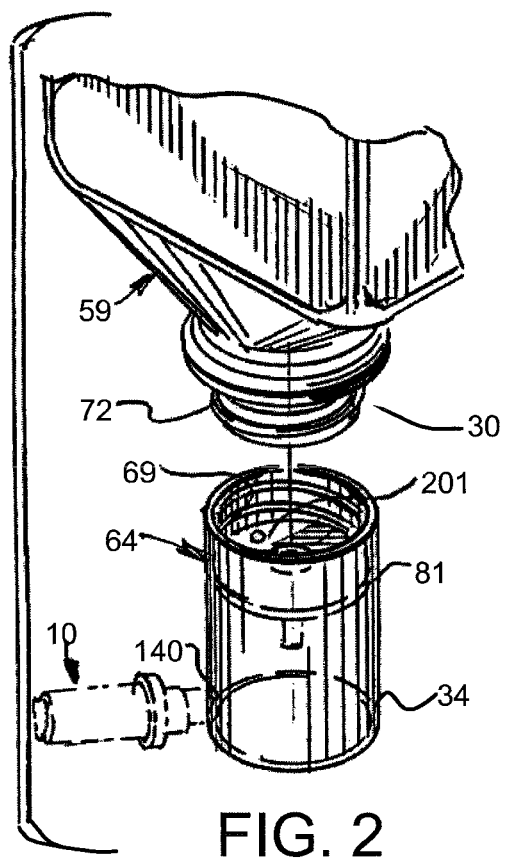
FIG. 2 is an exploded perspective view of the embodiment of FIG. 1, and further showing (in dotted lines) the structure of another preferred alternate embodiment using vacuum evacuation of irrigation fluid through a port situated near the plane of irrigation.
Figure 3:
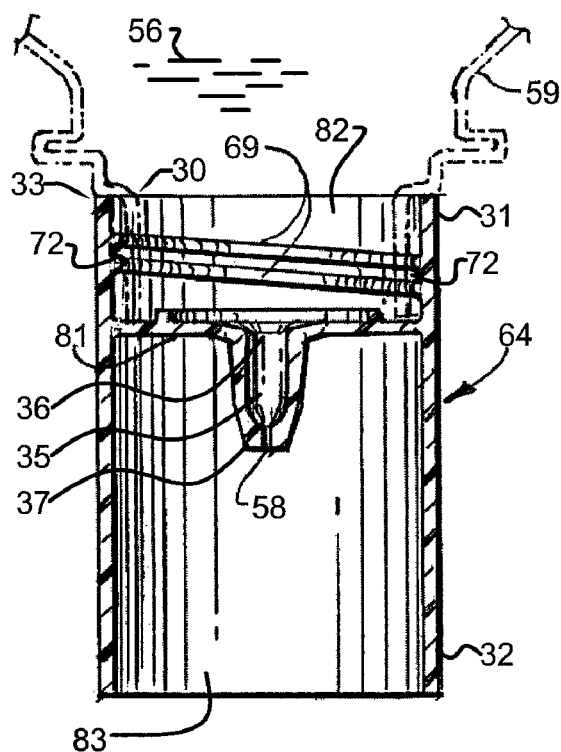
FIG. 3 is a sectional view of the embodiment of FIG. 1, illustrating details of preferred structure.

FIG. 2 shows a preferred embodiment of the present invention with wide mouth irrigation squeeze bottle 59 detached from splash shield 64. FIG. 3 is a sectional view of the embodiment of FIG. 1, illustrating details of a preferred structure. Preferably, splash shield 64 is transparent, as shown. Preferably, splash shield 64 comprises first end 31 and second end 32, as shown. Preferably, partition 81 divides first end 31 from second end 32, as shown. Preferably first end 31 comprises irrigation-source connector 33, as shown. Preferably, irrigation-source connector 33 comprises an inner diameter between about ⅘ inches and about 1¾ inches, most preferably between about 1.4 inches and about 1.6 inches, most preferably between about 1.3 inches and 1.6. Based on the type of connector desired, one may prefer an inner thread-to-thread diameter of about 1.3 inches over about 1.4 inches in cases where a thicker thread is desired. Preferably splash shield 64, including irrigation-source connector 33, partition 81, and inner hollow 83, consist of one monolithic piece. Preferably splash shield 64 is sterile.

Preferably, irrigation-source connector 33 comprises threads 69, as shown. Preferably, threads 69 comprise helical threads, as shown. Preferably second end 32 comprises inner hollow 83 as shown. Preferably, bottle neck finish portion 30 of wide mouth irrigation squeeze bottle 59 comprises threads 72, as shown. Preferably, threads 72 comprise male threads, as shown. Preferably, threads 72 comprise helical threads, as shown (embodying herein a bottle structured and arranged to contain irrigation fluid, such bottle comprising, a neck, wherein such neck comprises external threads structured and arranged to connect with a bottle cap) structured and arranged to couple with threads 69 (such threads embodying herein threads structured and arranged to provide a threaded connection with the source of irrigation fluid; and further embodying herein wherein such threads comprise internal threads structured and arranged to connect with external threads on a neck of a irrigation fluid bottle; and further embodying wherein such irrigation-source connector comprises threads structured and arranged to provide a threaded connection; and further embodying herein an adapter structured and arranged to allow a connection between such body and such source of irrigation fluid) within inner hollow 82 of splash shield 64 to form a tight connection. Preferably, irrigation-source connector 33 is structured and arranged to connect to standard wide mouth wound irrigation squeeze bottles, such as, for example, those manufactured by BAXTER, ABBOT, or MCGAW. Upon reading the teachings of this specification, those with ordinary skill in the art will now understand that, under appropriate circumstances, considering such issues as cost of manufacture, compatibility, market demand, etc., other connection arrangements, such as, for example, non-helical threads, female threads, luer-type connections, non-threaded connections, snap on connections, etc., may suffice.

Preferably, partition 81 comprises orifice nozzle 58 for directing a stream of fluid from the irrigation source (such as, for example, wide mouth irrigation squeeze bottle 59) toward flesh 53 (embodying herein a body, having a first end and a second end wherein such first end is open to a first hollow portion of such body and such second end is open to a second hollow portion of such body; an irrigation-source connector structured and arranged to connect such body, adjacent the first end, to a source of irrigation fluid; a partition, between such first hollow portion and such second hollow portion; wherein such partition comprises at least one nozzle structured and arranged to direct at least one stream of the irrigation fluid towards the wound; wherein such splash shield system is structured and arranged in such manner as to protect the user from contact with the irrigation fluid; and further embodying herein wherein such adapter comprises a nozzle structured and arranged to direct a stream of the irrigation fluid towards the wound).

Preferably, nozzle 58 protrudes from partition 81, as shown. Preferably, nozzle 58 protrudes from partition 81a distance between about 0.005 inches to about 1 inch, as shown. Preferably nozzle 58 comprises at least one passageway 35 with at least one cross-sectional area, that decreases from at least one inlet port 36 of said at least one nozzle to at least one outlet port 37 of said at least one nozzle, forming at least one venturi passageway 35, as shown. Preferably, the length of passageway 35 is between about 0.005 inches to about 1 inch.

Preferably, splash shield 64 comprises a cylindrical exterior wall portion 34 (see FIG. 2), as shown, wherein "cylindrical", as used throughout this specification, is defined in the broad mathematical sense as a surface traced by a straight line moving parallel to a fixed straight line and intersecting a fixed planar closed curve. Preferably cylindrical exterior wall portion 34 is substantially round. Preferably inner hollow 83 comprises a substantially round cylindrical portion, as shown (embodying herein a body having a first end and a second end, and a cylindrical exterior wall and irrigation-source connector structured and arranged to connect such body, at such first end, to a source of irrigation fluid; wherein such body comprises at least one inner hollow; wherein such second end, is open to such at least one inner hollow; wherein such splash shield system is structured and arranged in such manner as to protect the user from contact with the irrigation fluid; and further embodying herein wherein such cylindrical exterior wall is substantially round; and such at least one inner hollow comprises a substantially round cylinder). Upon reading the teachings of this specification, those with ordinary skill in the art will now understand that, under appropriate circumstances, considering such issues as intended use, user preference, cost of manufacture, etc., other splash shield shape arrangements, such as, for example, non-cylindrical portions, conical shaped portions, asymmetrical shaped portions, etc., may suffice.

According to the preferred embodiment shown in FIG. 1, there is preferably a single nozzle for irrigating flesh 53 with fluid 56, as shown. According to the preferred embodiment shown in FIG. 2, partition 81 preferably comprises at least one additional hole 201 to facilitate irrigating flesh 53 with multiple streams of fluid 56 (wherein such partition further comprises, at least one hole through such partition (in addition to such nozzle)). Thus, when bottle 59 is attached and squeezed, fluid 56 is forced into and through orifice nozzle 58 (and also, through hole 201), as shown.

FIG. 2 also shows (in dotted lines) the structure of another preferred alternate embodiment using vacuum evacuation of irrigation fluid by vacuum line 10 through a port 140 situated near (as shown) the plane of irrigation (embodying herein an output opening structured and arranged to allow suctioning excess irrigation fluid from within such body).

Using the invention with a standard wide mouth irrigation bottle with a port approximately the size of a luer tip opening, one can generate a pressure similar to that of the outer diameter of an 18-gauge needle. Though this may seem counterintuitive to some, this larger luer sized opening has a diameter approximately 4 times the size of the smaller 18-gauge sized opening, and it is capable of generating a similar peak irrigation stream pressure.

Although fluid discharge ports larger than 1.5 mm can provide advantages, fluid discharge ports larger than 4 mm may have disadvantages. Beyond a certain point the diameter of the fluid discharge port may become too large. The diameter of the port may become so large that fluid from the stream is wasted. For example, a stream of a diameter of more than 4 mm would waste a lot of fluid irrigating a more narrow laceration of 1 mm. Beyond a certain width a port that is too wide might not be able to generate the desired irrigation pressures using a standard manual squeeze bottle. 4 mm is the approximate size of catheter tip piston syringe openings. Catheter tip plunger syringes have been shown to generate a pressure of at least 4 psi.

In the medical literature there is much debate over the ideal pressure to irrigate a wound. For eye wounds it is desirable to limit the pressure, but increase the volume of fluid. For wounds treated in the hospital and clinic setting, some authors recommend at least 4 psi and others recommend at least 7 psi. Some recommend no more than 8 psi of pressure and other recommend no more than 15 psi of pressure. Typically in the operating room higher pressure devices are used. In chronic wound care settings frequently low pressures are used. The ideal medical irrigation device or method is one that is simple, inexpensive and can achieve a variety of different pressure ranges and allows the user to choose the pressure or range which they judge to be optimal.

When using devices with that generate higher pressured streams it is desirable to have an adequately sealed system to permit more efficient generation of pressures without loss of pressure through leaks. Leakage would require more energy to be used to generate a higher pressure in the system and therefore of the irrigation stream. In the case of manually squeezed irrigation bottle, leakage of the system may make some pressures unattainable by manual pressure that otherwise would have been attainable.

Another problem with leakage of manually squeezed irrigation bottle system is that the leaks may cause irrigation fluid to drain or spray out around the collar of the wide mouth irrigation bottle connector. Along with reducing the pressure achievable in the system, such a leakage may cause a messy situation. Fluid may drip on the outside of the irrigation shield. If the shield is transparent, the leaked fluid drops or streaks may obstruct the view through the transparent splash shield.

It is therefore desirable to have a shielded irrigation device that has a liquid tight seal on at least one irrigation bottle finish.

Figure 4:
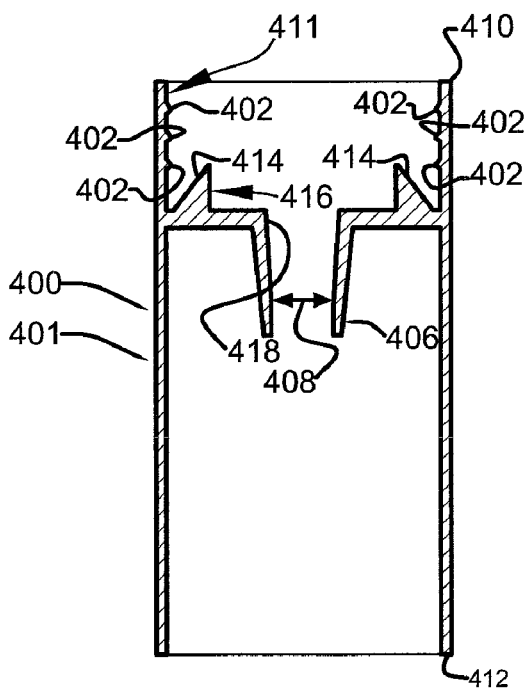
FIG. 4 is a sectional view through another preferred embodiment of a splash shield system according to the present invention.

FIG. 4 is a sectional view through splash shield 400. Preferably, splash shield 400 comprises body 401, as shown. Preferably, body 401 consists essentially of one unitary, monolithic piece, as shown. Preferably, body 401 comprises transparent plastic. Preferably, transparency provides minimal distortion and maximum clarity so that the wound can be easily viewed through body 401 (allowing the user to accurately aim the irrigation stream). Preferably, the irrigation of the wound can be easily viewed from the side of transparent body 401 or from above body 401. Maximum clarity can generally be achieved more effectively with rigid material. Preferably, body 401 comprises first end 410 and second end 412, as shown. Preferably, first end 410 comprises irrigation source connector 411 (at least embodying herein at least one squeezable wide mouth irrigation fluid bottle connector structured and arranged to connect such at least one body), as shown. Splash shield 400 caps a wide mouth irrigation fluid bottle when connected to a wide mouth irrigation fluid bottle. Preferably, second end 412 comprises inner hollow 404, as shown. Preferably, second end 412 comprises at least one transparent portion. Preferably, first end 410 is in fluid communication with second end 412 via fluid discharge port 418 (also sometimes referred to herein as an irrigation fluid port), as shown. Preferably, fluid discharge port 418 comprises nozzle 406. Preferably, nozzle 406 protrudes into inner hollow 404, as shown. Preferably inner hollow 404 is structured and arranged to assist in containing fluid which is discharged from fluid discharge port 418 into inner hollow 404, as shown. Preferably, inner hollow 404 may temporarily contain greater than 25 ml of irrigation fluid when second end 402 is placed adjacent the flesh of a patient. Since a wide mouth irrigation fluid bottle dispenses a larger volume of irrigation fluid than, for example, a 20 cc handheld syringe, a larger shield capable of temporarily containing such volume of greater than 25 ml is preferred to properly irrigate the wound of a patient. It is desired that the volume of the shield be sufficient to contain a volume, temporarily, when the splash shield is adjacent the flesh or body surface of a patient so that a large volume of irrigation fluid from a large area fluid port may flow to irrigate a wound. A large fluid port preferably has a large area for discharge of fluid. For purposes of this disclosure, a large area fluid port is greater than a port having a diameter of 1 mm. Preferably, such fluid port has a diameter of 1.5 mm. A further advantage of the larger volume inner hollow is that it permits a user to direct irrigation fluid to a wound. When using 20 cc syringe to irrigate a wound, constant refilling is necessary to apply large volumes. This is inefficient when time may be of the essence in emergency care situations. If the inner hollow volume is too small, insufficient irrigation fluid will reach the wound and will diminish the protective effect of the splash shield because, for example, the low volume splash shield will need to be raised to accommodate further irrigation fluid. The height of inner hollow 404 may also be important in providing a user with a reasonable and comfortable way to look through the shield of splash cap 400 when the splash cap 400 is connected to a wide mouth irrigation squeeze bottle, inverted, and used to irrigate a wound. Preferably, inner hollow 404 helps protect a user from fluid that is discharged from fluid discharge port 418 and splashing fluid that results when the fluid impacts the wound (contaminated irrigation fluid), etc. Preferably, fluid discharge port 418 has a diameter 408 of at least 1.5 mm. Preferably, fluid discharge port 418 has a diameter 408 of at least 2 mm. Preferably, fluid discharge port 418 has a diameter 408 of at least 2.5 mm.

Figure 5:
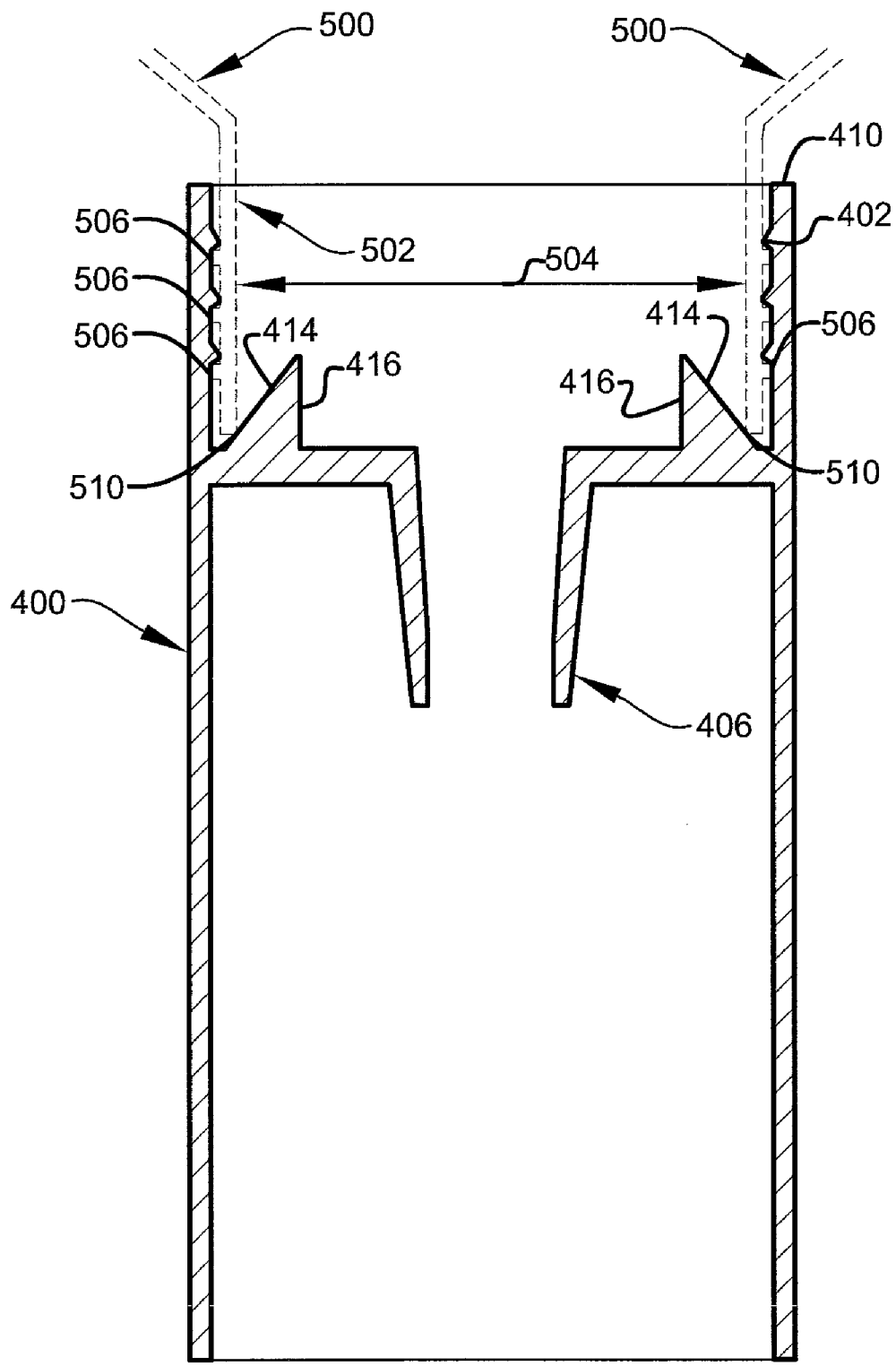
FIG. 5 is an enlarged view of the embodiment of FIG. 4 attached to a bottle (which is in dotted lines) with a wide inner diameter bottle finish.
Figure 6:
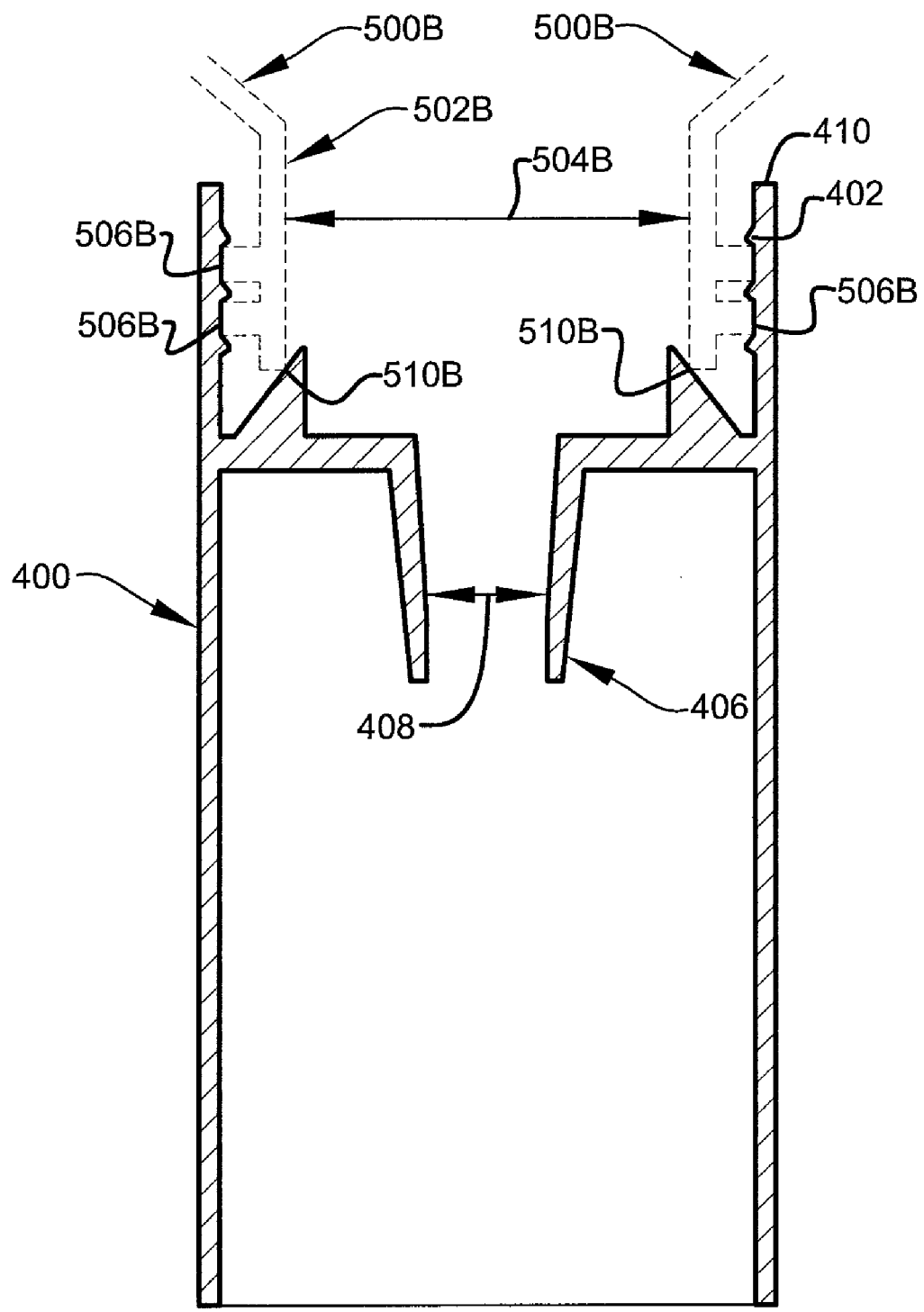
FIG. 6 is an enlarged view of the embodiment of FIG. 4 attached to a bottle (which is in dotted lines) with an inner diameter bottle finish narrower than the bottle of FIG. 5.

Preferably, irrigation source connector 411 is structured and arranged to accommodate a range of bottle finish sizes. Comparing FIG. 5 and FIG. 6, it can be seen how splash shield 400 can accommodate attaching to wide mouth irrigation squeeze bottles with different sized bottle finish portions. FIG. 5 shows splash shield 400 connected to bottle 500 with a relatively wider diameter bottle finish inner diameter 504, as shown. FIG. 6 shows splash shield 400 connected to bottle 500B with a relatively narrower diameter bottle finish inner diameter 504B, as shown.

Referring to FIG. 5, preferably, irrigation source connector 411 comprises threads 402, as shown. Preferably, threads 402 are structured and arranged to provide a threaded connection with threads 506 on the bottle finish 502 of a wide mouth wound irrigation squeeze bottle 500. Preferably, threads 402 have standard thread dimensions. Preferably, threads 402 comprise 1½-6 UNC thread dimension. Preferably, threads 402 comprise 1½-6 UNC coarse thread dimension. Preferably, threads 402 comprise helical threads with at least 2 turns, more preferably at least 2.5 turns. Less than 2 turns increases the likelihood of cross threading problems, and is therefore less preferable. More than 2.5 turns helps prevent cross threading and improves universal sealing to a variety of different sized bottle finishes (such as the different dimensions of bottle finishes for standard wound irrigation squeeze bottles manufactured by BAXTER, ABBOT, and MCGAW.

Preferably, irrigation source connector 411 is structured and arranged to provide a liquid-tight seal so that when an irrigation source (e.g. a wide mouth wound irrigation squeeze bottle) is attached to the irrigation source connector 411, fluid can only escape through the fluid discharge port 418 (and fluid cannot escape through the connection, threads, etc.). Preferably, irrigation source connector 411 comprises ridge 416, as shown. Preferably, ridge 416 comprises ridge outer surface 414, as shown. Preferably, ridge outer surface 414 is structured and arranged to seal against the inner diameter of a bottle neck finish portion. Preferably, ridge 416 is shaped with an external taper (slant/slope), as shown. Ridge 416 permits a liquid-tight seal without relying on resilient material so that splash shield 400 can be manufactured as one monolithic piece of rigid material to reduce cost. Preferably, liquid-tight seal 510 is achieved by contact between the inner diameter of the bottle finish and outer surface of ridge 416, as shown. Preferably, seal 510 is achieved by screwing splash shield 400 onto wide mouth wound irrigation squeeze bottle 500 (by engagement between threads 506 and threads 402) until the end of bottle finish 502 seats tightly on ridge outer surface 414 of ridge 416, as shown. Preferably, irrigation source connector 411 is structured and arranged so that seal 510 (and seal 510B, etc., for other size bottle finishes) remains liquid-tight (preventing leaking of fluid) at pressures of 4 pounds per square inch, preferably remaining liquid-tight at pressures of 7 pounds per square inch.

Comparing FIG. 5 and FIG. 6, it can be seen that for relatively wider diameter bottle finish inner diameter 504 (see FIG. 5), seal 510 occurs nearer the base of ridge 416 (where the ridge outer surface diameter is larger compared to the top). Whereas, for relatively narrower diameter bottle finish inner diameter 504B (see FIG. 6), seal 510B occurs nearer the top/apex of ridge 416 (where the ridge outer surface diameter is smaller compared to the base). Preferably, ridge outer surface 414 has a range of ridge outer surface diameters from greater than 1.2 inches near the base, to less than 1.14 inches near the top/apex of ridge 416, as shown. Preferably, irrigation source connector 411 is structured and arranged to accommodate and provide a liquid-tight seal for a range of bottle finish sizes. Preferably, irrigation source connector 411 is structured and arranged to universally fit and provide a liquid-tight seal for the different bottle finish dimensions of standard wound irrigation bottles manufactured by BAXTER, ABBOT, and MCGAW. It is noted that BAXTER standard wound irrigation bottles typically have an inner diameter of about 1.14 inches, while ABBOT standard wound irrigation bottles typically have an inner diameter of about 1.17 inches, and MCGAW standard wound irrigation bottles typically have an inner diameter of about 1.2 inches. By being able to universally fit any of the top three most popular manufacturers mentioned above, splash shield 400 is more convenient and efficient than a product that would only fit one specific bottle size. Further, splash shield 400 perferably fits to standard squeezable wide mouth irrigation fluid pour bottles which are designed to have an inner lip in addition to their wide mouth diameter to avoid irrigation fluid dripping while pouring such standard bottles.

According to an alternate preferred embodiment of the present invention ridge 416 comprises resilient material. According to another alternate preferred embodiment of the present invention ridge 416 can be supplemented and/or replaced by a washer, preferably made of resilient material, in order to achieve a liquid tight seal.

Figure 7:
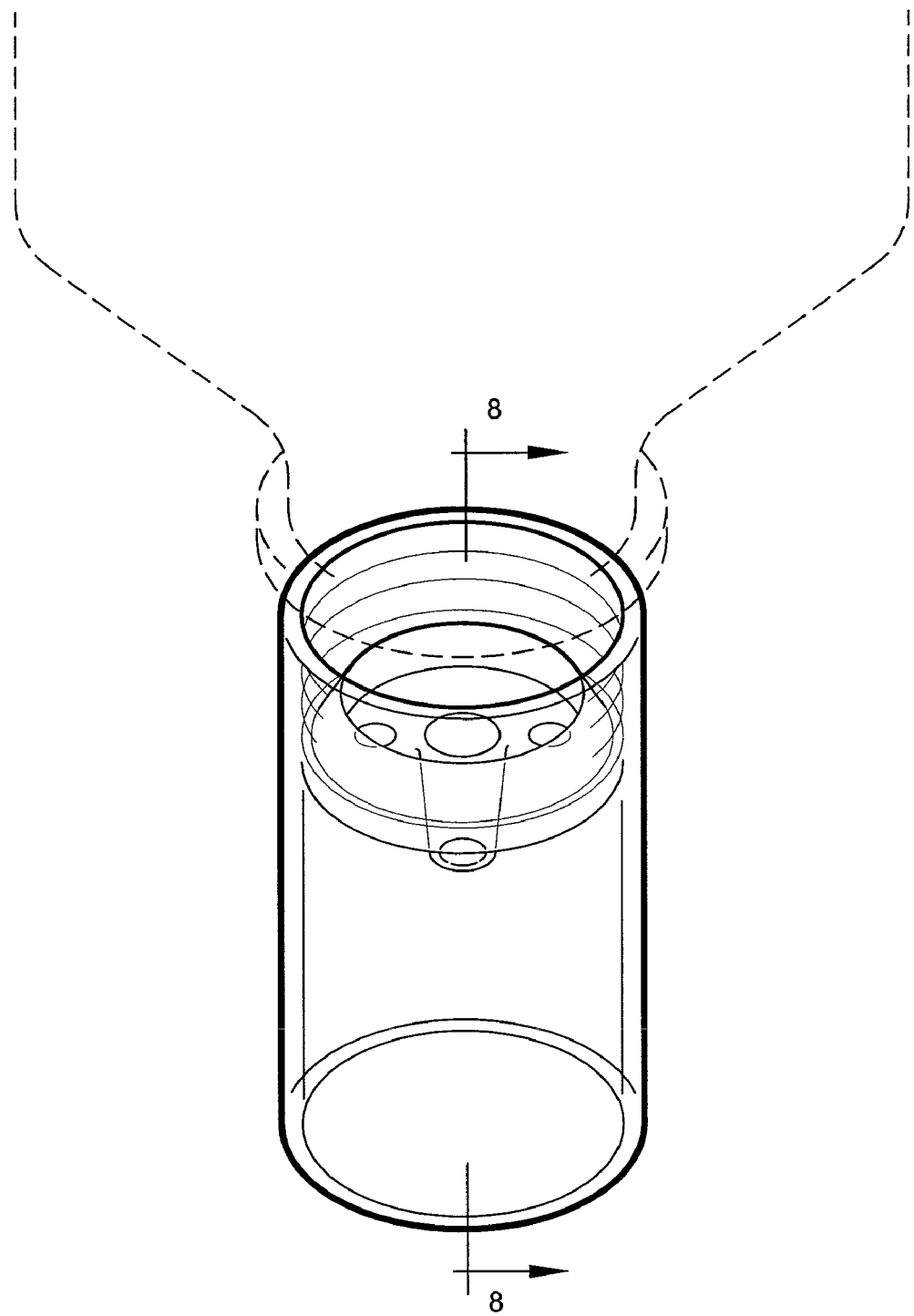
FIG. 7 shows a perspective view showing an alternate preferred embodiment of a splash shield system with multiple irrigation fluid discharge ports.

FIG. 7 shows a perspective view showing an alternate preferred embodiment of a splash shield system with multiple fluid discharge ports.

Figure 8:
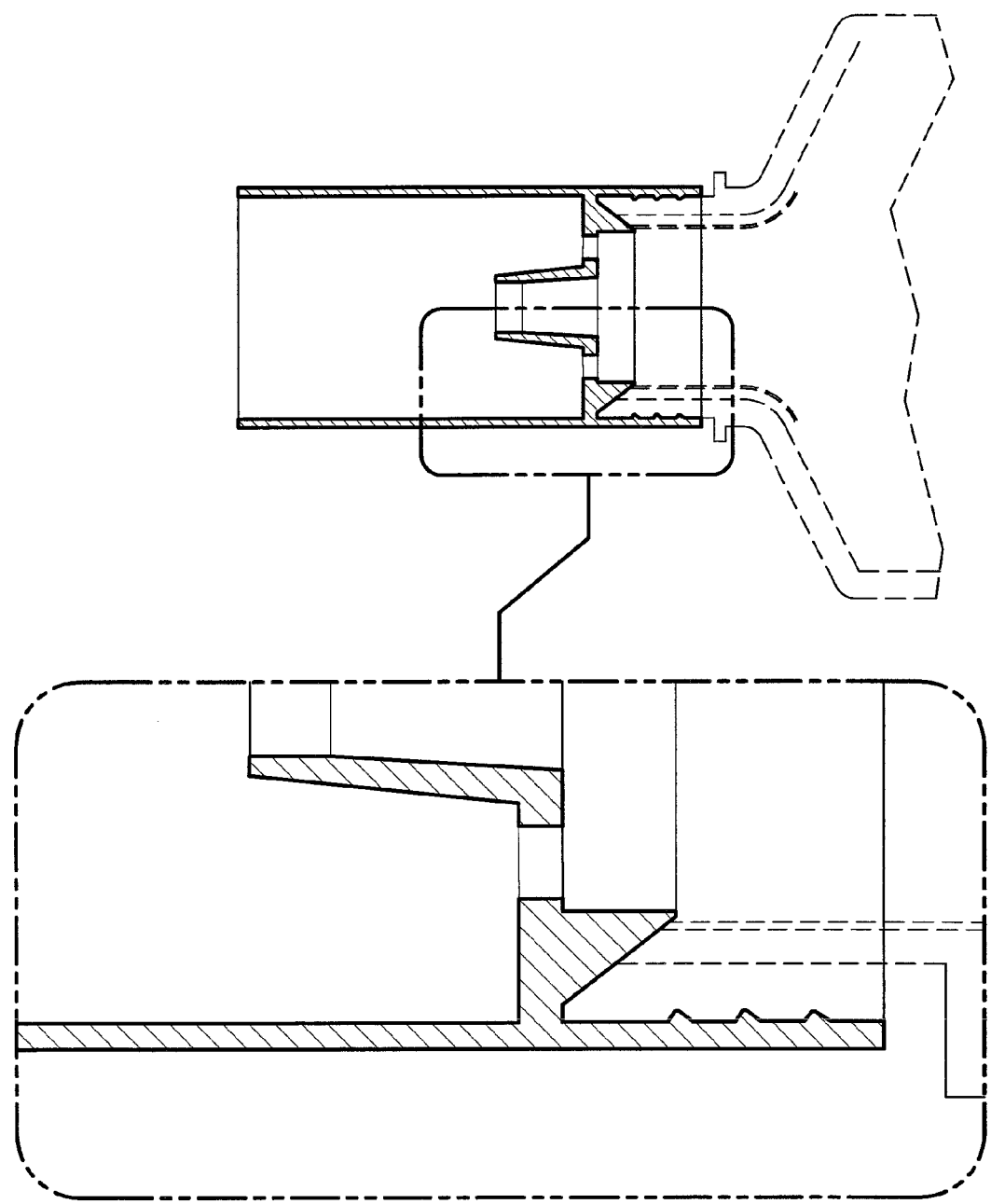
FIG. 8 shows a sectional view and a blowup detail sectional view through the section 8-8 of FIG. 7.

FIG. 8 shows a sectional view and blowup detail sectional view of the embodiment of FIG. 7.

Figure 9:
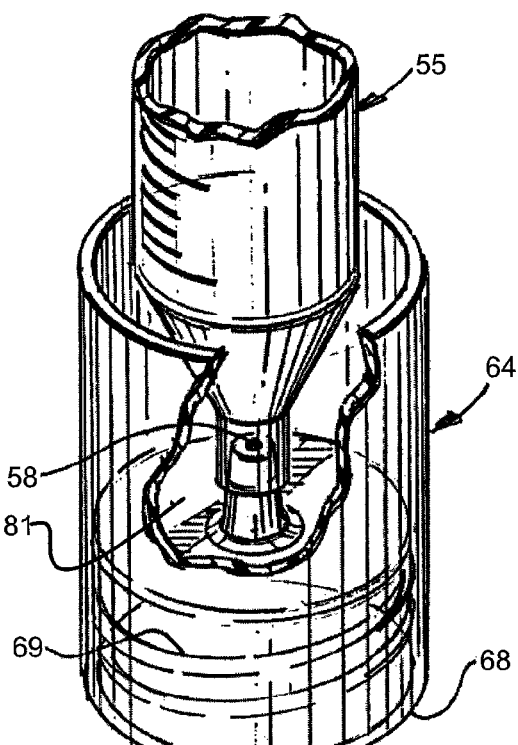
FIG. 9 is a perspective view illustrating the use of the splash shield of FIG. 1, inverted for use with a syringe.
Figure 10:
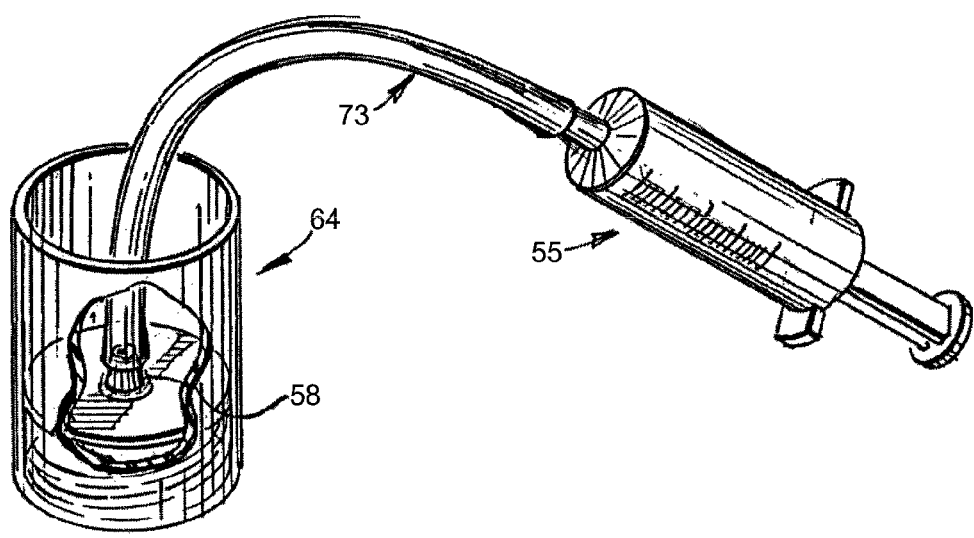
FIG. 10 is a perspective view illustrating the use of the splash shield of FIG. 9 using a syringe with connecting tubing.

FIG. 9 is a perspective view illustrating the use of the splash shield 64 of FIG. 1 inverted for use with a syringe 55. In this embodiment, the open unthreaded end of splash shield 64 receives a syringe 55 whose nozzle fits over the now protruding (from the former underside of partition 81) part of orifice nozzle 58, as shown. Thus, when syringe 55 discharges its fluid, the threaded portion 68 of splash shield 64 now acts as a splash shield. Similarly, FIG. 10 is a perspective view illustrating the use of the splash shield 64 "upside down" arrangement of FIG. 9 using a syringe 55 with connecting tubing 73, which tubing 73 is in this case connected over the protruding orifice nozzle 58.

Figure 11:
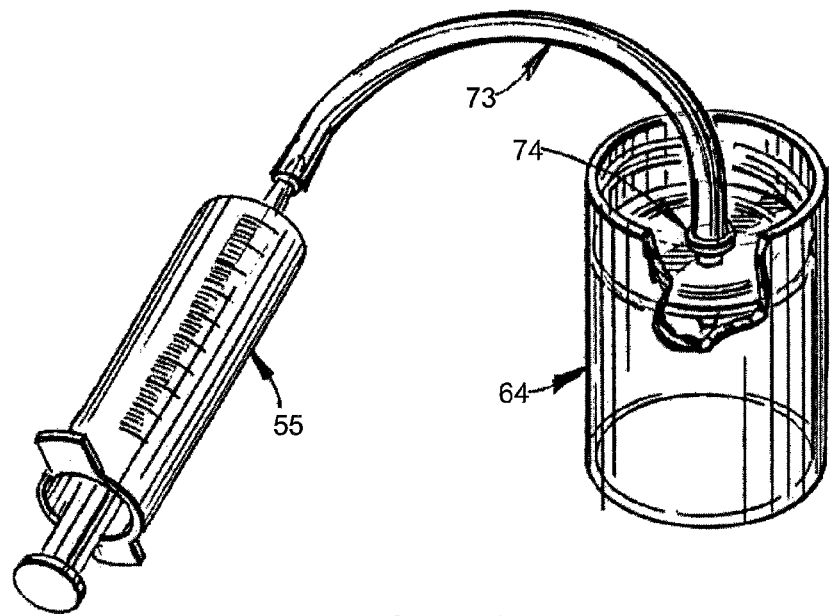
FIG. 11 is a perspective view illustrating the use of the splash shield of FIG. 1 using a syringe with connecting tubing and an adapter.
Figure 12:
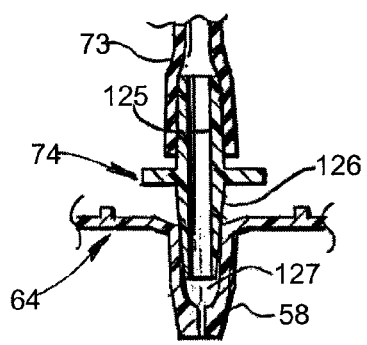
FIG. 12 is a sectional view of the adapter connection area of the embodiment of FIG. 11 illustrating the area detail.

FIG. 11 is a perspective view illustrating the use of the splash shield 64 of FIG. 1 using a syringe 55 with connecting tubing 73 and an adapter 74. FIG. 12 is a sectional view of the adapter 74 connection area of the embodiment of FIG. 11 illustrating the area detail. As shown, tubing 73 fits over an upper male portion 125 of the adapter 74 while a lower male portion 126 of the adapter 74 fits within the upper hollow 127 of orifice nozzle 58 (embodying herein wherein such adapter allows connection of such body to multiple varieties of such source of irrigation fluid). Preferably, upper hollow 127 also allows connection to an irrigation-source with a syringe tip (embodying herein wherein such irrigation-source connector further comprises at least one adapter structured and arranged to provide a connection to a syringe tip).

Figure 13:
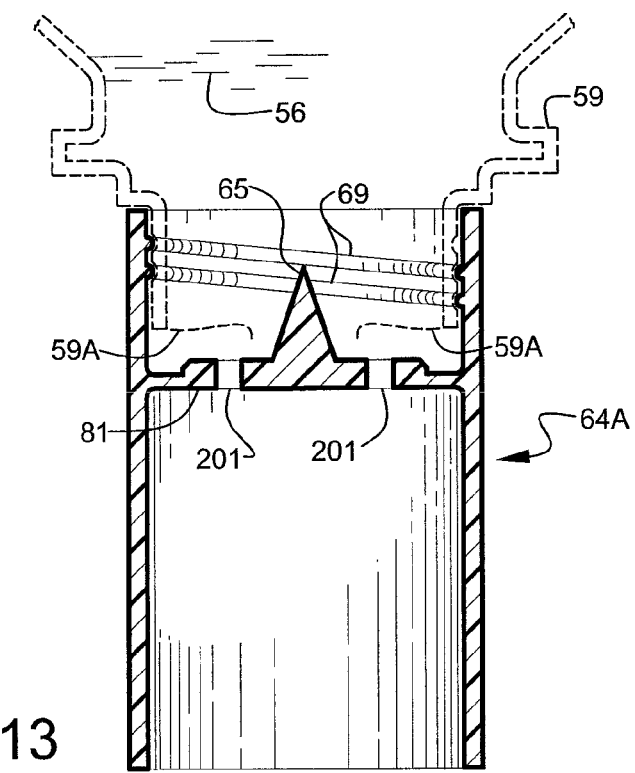
FIG. 13 is a sectional view of another preferred embodiment of a splash shield according to the present invention, showing a puncturing means for breaking the seal on a source of irrigation fluid.

FIG. 13 is a sectional view of yet another preferred embodiment of a splash shield 64A according to the present invention, meshed with an irrigation squeeze bottle 59, illustrating details of preferred structure. Preferably, splash shield 64A has a puncturer 65, as shown (embodying herein a body structured and arranged to assist in protecting a user from contact with irrigation fluid directed at a patient's wound; an irrigation-source connector structured and arranged to connect such body, at a first end of such body, to a source of irrigation fluid; wherein such irrigation-source connector comprises a puncturer structured and arranged to puncture at least one barrier between such body and the source of irrigation fluid and further embodying wherein such puncturer comprises a spike). As splash shield 64A is meshed with bottle 59, bottle membrane 59A (which acts as a barrier to fluid escaping the bottle 59) is punctured by puncturer 65, which permits fluid to exit from bottle 59. Below the threads 69 of splash shield 64A is internal partition 81 sealing the open/bottom end of splash shield 64A except for hole(s) 201. Preferably, puncturer 65 does not puncture bottle membrane 59A until after sufficient connection between the bottle 59 and the splash shield 64A is made to provide a sufficient seal preventing fluid from leaking from the meshed connection. Preferably, puncturer 65 punctures a bottle membrane 59A when the meshed connection between splash shield 64A and bottle 59 is already engaged, but not yet fully and completely seated, preferably when the meshed connection is approximately half-way complete. Thus, when bottle 59 is attached and squeezed, fluid 56 is forced into and through hole(s) 201.

Figure 14:
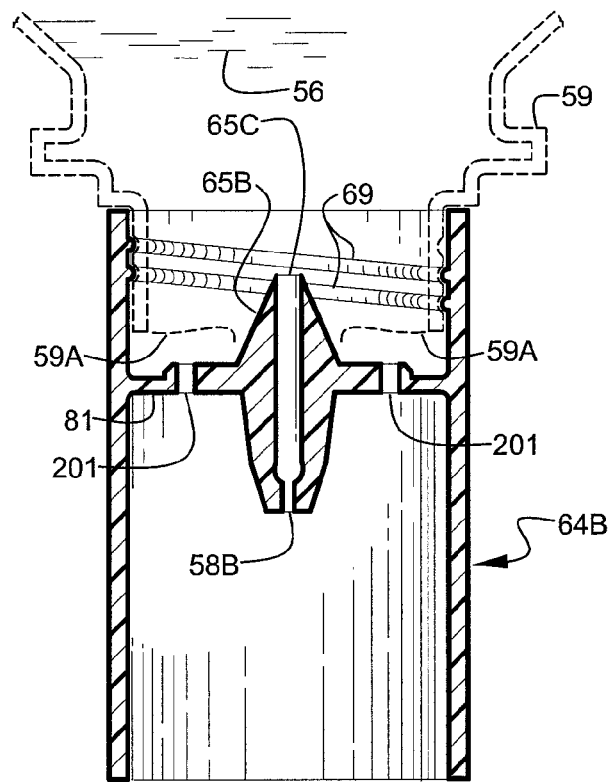
FIG. 14 is a sectional view of another preferred embodiment of a splash shield according to the present invention, showing a puncturing means with integral fluid transport means.

FIG. 14 is a sectional view of yet another preferred embodiment of a splash shield 64B according to the present invention, meshed with an irrigation squeeze bottle 59, illustrating details of preferred structure. Preferably, splash shield 64B has a puncturer 65B. As splash shield 64B is meshed with bottle 59, bottle membrane 59A is punctured by puncturer 65B, which permits fluid to exit from bottle 59. One or more fluid channel(s) 65C in puncturer 65B permits fluid 56 to exit from bottle 59 into orifice nozzle 58B (embodying herein wherein such spike comprises at least one opening structured and arranged to transport the irrigation fluid from the source of irrigation fluid to such body). Below the threads 69 of splash shield 64B is internal partition 81 sealing the open/bottom end of splash shield 64B except for orifice nozzle 58B for directing a stream toward flesh 53. It is noted, that one or more additional hole(s) 201 may be optionally found going through partition 81 in order to increase irrigation flow to a wound. Preferably, puncturer 65B does not puncture bottle membrane 59A until after sufficient connection between the bottle 59 and the splash shield 64B is made to provide a sufficient seal preventing fluid from leaking from the meshed connection. Preferably, puncturer 65B punctures bottle membrane 59A when the meshed connection between splash shield 64B and bottle 59 is already engaged, but not yet fully and completely seated, preferably when the meshed connection is approximately half-way complete. Thus, when bottle 59 is attached and squeezed, fluid 56 is forced through the fluid channel(s) 65C and through orifice nozzle 58 (and also, optionally, through optional hole(s) 201), as shown.

Figure 15:
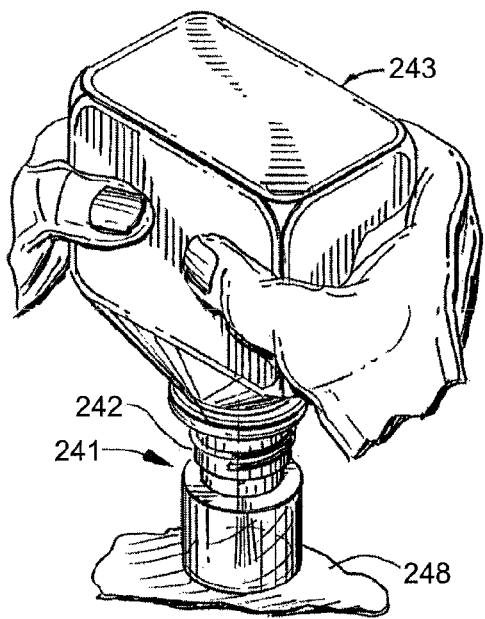
FIG. 15 is a perspective view of another preferred embodiment of a splash shield according to the present invention, which splash shield is shown fitted into the neck of a bottle of the type containing irrigation fluid.
Figure 16:
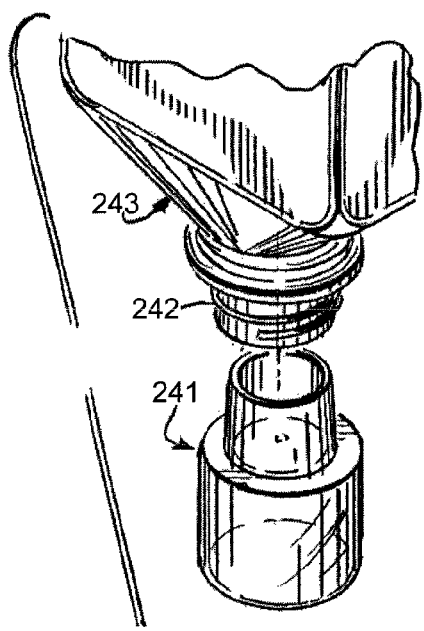
FIG. 16 is a perspective view of the embodiment of FIG. 15 shown detached from the illustrated bottle.
Figure 17:
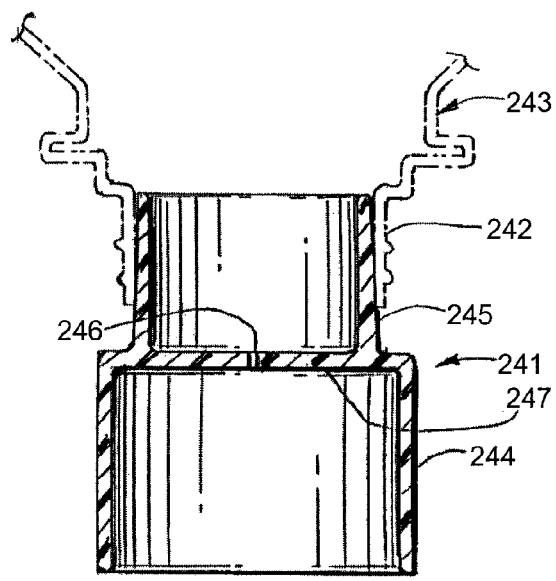
FIG. 17 is a sectional view through the center of the embodiment of FIG. 15 showing structural details and showing its fit in the illustrated bottle (which is in dotted lines).
Figure 18:
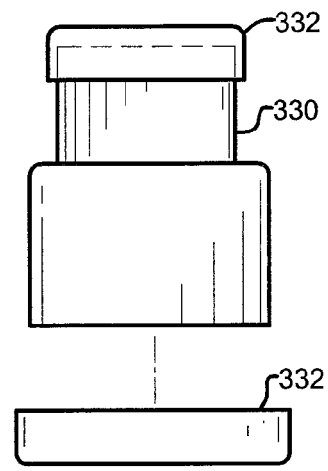
FIG. 18 is a side view of a splash shield with an end cap attached on the top end and an end cap detached from the bottom end of splash shield.

FIG. 15 is a perspective view of another preferred embodiment of a splash shield 241 according to the present invention, which splash shield 241 is shown fitted into the neck 242 of a bottle 243 of the type containing irrigation fluid. FIG. 16 is a perspective view of the splash shield 241 of FIG. 15 shown detached from the illustrated bottle 243. FIG. 17 is a sectional view through the center of the splash shield 241 of FIG. 15 showing structural details and showing its fit in the illustrated bottle 243 (which is in dotted lines). Splash shield 241 (as shown best in FIG. 17) is stepped from a larger-diameter cylindrical portion 244 to a smaller-diameter portion 245 that is sized with external taper to friction fit as shown within neck 242 of bottle 243 (in dotted lines in FIG. 17). Thus, for example, squeezing of a squeeze bottle 243 brings irrigation fluid into upper portion 245, from where it may be forced through a hole 246 in dividing surface 247 to impinge upon skin portion 248 (see FIG. 15) with lower portion 244 acting to shield say, a user, from fluid or debris from a wound on skin portion 248. FIG. 18 is a side view of a splash shield with an end cap 332 attached on the top end and an end cap 332 detached from the bottom end of splash shield 330. Preferably, end cap 332 assists in protecting internal sterility of the splash shield. End cap 332 also creates a closed pocket within splash shield, which can be used for example to store other items such as wound treatment products and devices.

Figure 19:
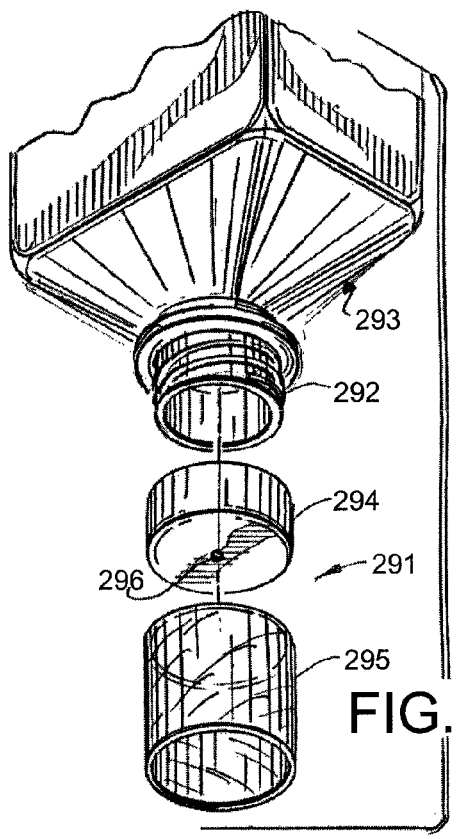
FIG. 19 is an exploded perspective view of yet another preferred embodiment of the splash shield of the present invention, showing the end of an irrigation bottle, a bottle adapter to control the irrigation stream, and a tubular splash shield element.
Figure 20:
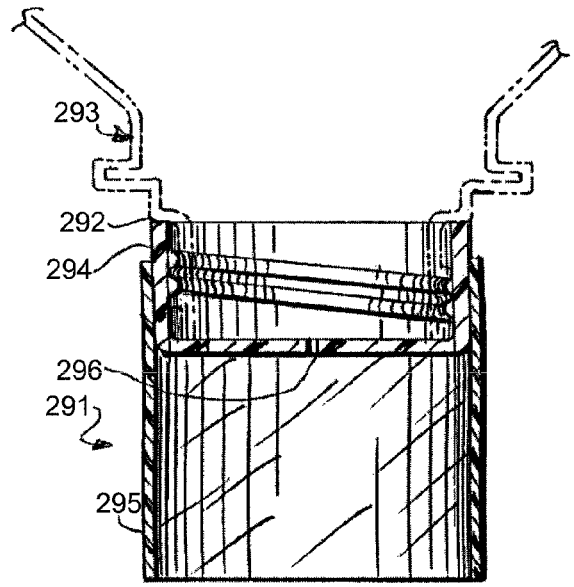
FIG. 20 is a sectional view of the embodiment of FIG. 19 illustrating the details with the splash shield connected to the bottle (shown in dotted lines).

FIG. 19 is an exploded perspective view of yet another preferred embodiment of the splash shield 291 of the present invention, showing the end 292 of an irrigation bottle 293, a bottle adapter 294 to control the irrigation stream, and a tubular splash shield element 295. FIG. 20 is a sectional view of the splash shield 291 of FIG. 19 illustrating the details with the splash shield 291 connected to the bottle 293 (shown in dotted lines). As shown, to use the splash shield 291, it is preferred to friction fit adapter 294 over the end 292 of bottle 293, and to friction fit splash shield element 295 over the bottom of adapter 294. Then fluid from bottle 293 may be forced into adapter 294, through hole 296, and into the tubular splash shield element areas for wound irrigation.

FIG. 21 is a perspective view of a preferred embodiment of a combined splash shield and irrigation squeeze tube 301 according to the present invention. FIG. 22 is a partial perspective view of the irrigation squeeze tube 301 of FIG. 21, partially cut away to show its use with cap 302 removed. Toothpaste-type squeeze tube portion 299 has a built-in or a removable transparent wound irrigation shield portion 303. An outlet 304 to allow fluid egress or to allow attachment to a vacuum source (not shown) may be optionally provided for the advantages enumerated previously. Cap 302 is made long enough for removal or attachment to tube portion 299 with shield portion 303 in place. In operation, the tube portion 299 is squeezed, thus forcing irrigation fluid onto a wound, as previously set forth generally. Having a removable shield portion 303 is preferred if cap 302 is to be provided with nozzle 305 adaptations or adaptors (as taught previously herein) that allow modulation and that must be accessed easily in a sterile fashion, particularly if a simple, cheap, and easily available component such as a transparent plastic PVC tubing were used.

FIG. 23 a is front view illustrating yet another preferred embodiment of a splash shield 271 according to the present invention, showing a spike connector 272 attached to a squeeze bag 273 and also fitted into a cylindrical splash shield element 274. FIG. 24 is a perspective view of the splash shield 271 of FIG. 23, showing the spike connector 272 separated from the cylindrical splash shield element 274. FIG. 25 is a partial sectional view showing the connection details with the spike connector 272 attached to the cylindrical splash shield element 274. Spike connector 272 is a component of the type commonly used in creating an IV spike dripping chamber for modulating the administration of IV fluid through IV tubing, as shown (embodying herein wherein such spike comprises an IV-spike connector, unitary with such body). Splash shield element 274 may be made from standard PVC tubing to create an easily produced IV spike connector wound irrigation splash shield 271. By using simple available components in a new configuration and method, the tool investment would be minimized. It would also provide users with familiar equipment and parts that would reduce apprehension over using a new device. Providing this splash shield 271 permanently connected would provide significant advantages in some situations as described above. There may be an optional outlet contour or aperture 275 (see FIG. 24) which can function as an exit opening for effluent irrigation fluid or for the attachment of a vacuum connector. In addition, the tubing comprising splash shield element 274 may be flexible to prevent discomfort and trauma and to facilitate a better seal against the skin. When splash shield 271 is connected to bag 273, squeezed irrigation fluid 276 is forced through spike conduit 277 and through hole 278 in dividing surface 279, from where it enters attached splash shield element 274 for the described usages in wound irrigation.

FIG. 26 is an exploded perspective view of yet another preferred embodiment of the splash shield 281 of the present invention, showing a syringe-type tip 282, a syringe adapter 283 to control the irrigation stream, and a tubular splash shield component 284. FIG. 27 is a sectional view of the splash shield 281 of FIG. 26 illustrating the details with the parts connected. This arrangement provides a separate transparent shield component 284 which may be connected over a syringe body 285 to easily and quickly transform a standard syringe into a shield wound irrigation delivery device as shown in FIG. 27. One might want optionally to add adaptor 283 to the syringe tip 282 to modulate the flow. Providing a removable wound irrigation splash shield component 284 over the syringe body 285 would facilitate this by eliminating the need to reach into a potentially narrow, tight fitting sterile space to manipulate, position and exchange connectors.

FIG. 28 is a perspective view of yet another preferred embodiment of a splash shield 251 according to the present invention shown attached to an IV-type squeeze bag 252 by way of the IV spike connector 253 of splash shield 251. FIG. 29 is an enlarged (over FIG. 28) perspective view of the splash shield 251 of FIG. 28. FIG. 30 is sectional side view of the splash shield 251 of FIG. 28 illustrating the structural details thereof. FIG. 31 is a bottom view of the splash shield 251 of FIG. 28. Wound irrigation splash shield 251 is preferably transparent and engineered to be sterilizable and disposable as is commonly done in the medical industry. IV spike connector 253 (resembling a commonly available "IV spike") is a male connector with an inner conduit 254 for fluid 255 and a tapered pointed end 256 fits into the outlet end connector 257 of a fluid container such as a sterile IV solution bag 252 as shown in FIG. 28. Optionally, if desired, there might be an outlet 258 (dotted lines in FIG. 29) for the attachment to a vacuum source. In operation, fluid 255 is squeezed though conduit 254 of IV spike connector 253, from where it is forced through hole 259 of dividing surface 260 to form an irrigation stream through shield portion 261 (preferably shaped as shown, where, to better cover body wounds on appendages, as before mentioned, the preferred ratio of a maximum length of the open bottom end compared to a maximum width of such bottom end is at least 1.5:1.0) of wound irrigation splash shield 251. As shown, it is preferred that one (bottom) edge of the shield portion 261 be substantially linear so to provide a stable pivoting surface to promote a linearly directed irrigation stream. Also, one side 262 of shield portion 261 may preferably be substantially planar so as to increase the user's visibility of the irrigation process. Also, the irrigation stream may preferably be "off-center" to promote proximity to wall surfaces; that would allow better visualization. Also, it is preferred to provide a ledge 263 as shown at the bottom of shield portion 261 for better sealing against a skin portion when desired and for increasing the protective area of the device without increasing the width of the splash area required to form a seal.

FIG. 32 is a side elevation view of a preferred embodiment of the medical splash shield device 52 of the present invention. Preferably the device may be made of an inexpensive disposable transparent biocompatible medical grade plastic such as a US FDA class VI PVC or polycarbonate that may also be sterile to prevent wound infection. FIG. 33 is a top plan view of the splash shield device 52 of FIG. 32. FIG. 34 is a perspective view of the splash shield device 52 of FIG. 32 showing it in a restrained position, as on a portion of nearby equipment 19. FIG. 35 is a side sectional view of the splash shield device 52 of FIG. 32, illustrating its operation. As shown, the medical splash shield device 52 of this preferred embodiment includes proximal outlet 14 (embodying herein an output opening structured and arranged to allow suctioning excess irrigation fluid from within such body; wherein such output opening is structured and arranged to draw excess irrigation fluid from such splash portion toward a location approximately at a position symmetrically opposed (with respect to such maximum height dimension) from the location of such input opening), and a distal opening 17 for entry of the wound-washing fluid, shown as irrigation fluid 57. Preferably, distal opening 17 is located substantially lower than the maximum height dimension, as shown. The smooth rounded body 50 has an opening, as shown, which is either rectangular with rounded ends or a similar long oval in shape (seen most clearly in FIG. 33). Most of the illustrated bottom opening is portion 67 in a flat plane; but the distal end portion 51 of the bottom opening is in a plane coming upwards from the plane of portion 67 at about an angle of 30 degrees, as shown. A clip restraint 23 is preferably located near the top of the body 50 and protruding from the body 50 at about a parallel relationship to the protrusion of outlet 14. As shown, the proximal end wall 70 of body 50 is relatively vertical while the distal end wall 71 of body 50 rises very gradually at no more than about 45 degrees from the horizontal. The outlet 14 is located near the bottom-opening portion 67 and near the bottom of substantially vertical proximal end wall 70. The distal opening 17 preferably functions as an inlet and is located approximately centrally on the distal end wall 71.

Figure 36:
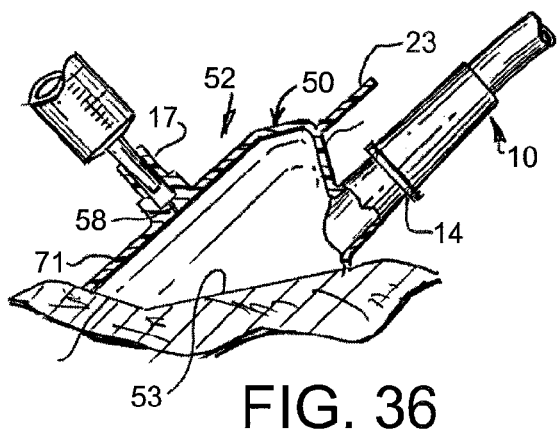
FIG. 36 is a side sectional view of the embodiment of FIG. 32, further illustrating operation with relief closure.

With reference to FIG. 35, the described preferred geometry permits the following operation (as shown) of splash shield device 52. The problems of prior art splash shield devices are overcome with the embodiment of FIGS. 32-36. The flushing irrigation fluid 57, as from syringe 55, irrigates wound 54 with a flow that flushes the debris toward and into vacuum line 10 by way of inlet end 12. Note that the placement of inlet end 12 near the flesh 53 portion of the splash shield device 52 assists in an efficient unidirectional flush flow to efficiently clean the wound 54 and remove debris and excess fluid (as shown). Preferably distal opening 17 is angled to assist in directing irrigation fluid at an oblique angle from vertical, so that a greater horizontal component of force from the fluid is imparted to flush debris out of the wound (embodying herein wherein such input opening is structured and arranged to assist in directing irrigation fluid at an oblique angle from vertical). Also, the elongated bottom shape (in an appropriate size) is more suited than a circular bottom shape for shielding and collecting flushing fluids on non-flat body parts such as arms, fingers, and feet. It is also noted that the relief afforded by the raised portion 51 of the shield bottom assists in providing more air flow (from an efficient direction) as needed for good flushing. And, as illustrated by FIG. 36 (a side sectional view of the embodiment of FIG. 32), the user may still press the splash shield device 52 toward the flesh 53 to operate the shield with relief closure as desired. This non-flat contour also assists in the pivoting of the device and the irrigation jet along the wound 54, changing the angle of the jet in relation to a position or location on the skin in a linear fashion.

Figure 37:
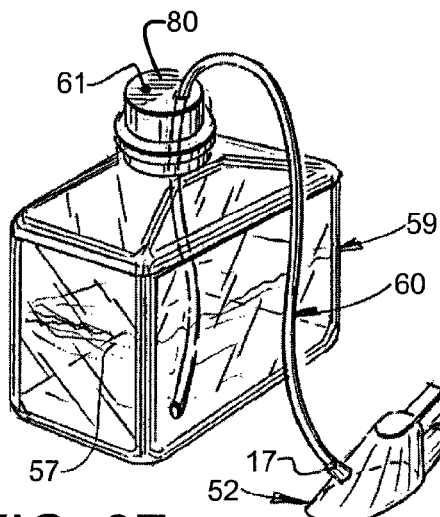
FIG. 37 is a perspective view of a preferred alternate usage of the splash shield of the type of FIG. 32, further illustrating siphoning of irrigation fluid from a fluid container.

FIG. 37 is a perspective view of a preferred alternate usage of the splash shield device 52 of the type of FIG. 32, further illustrating siphoning of irrigation fluid 57 from a fluid bottle 59 by way of tubing 60. Vent opening 61 is preferably provided in container cap 80 for well-known reasons.

Figure 38:
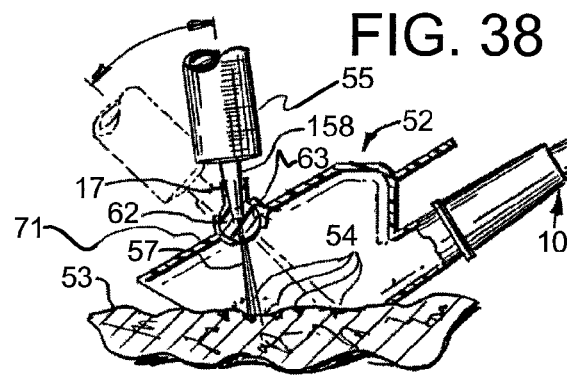
FIG. 38 is a side sectional view of an alternate preferred embodiment of the splash shield of the present invention, illustrating its operation incorporating an inlet swivel structure.
Figure 39:
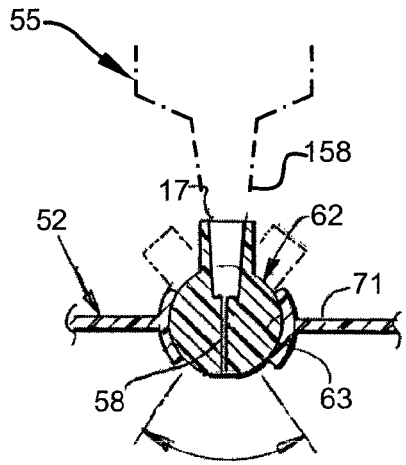
FIG. 39 is a partial expanded sectional view of the embodiment of FIG. 38, illustrating swivel detail.
Figure 40:
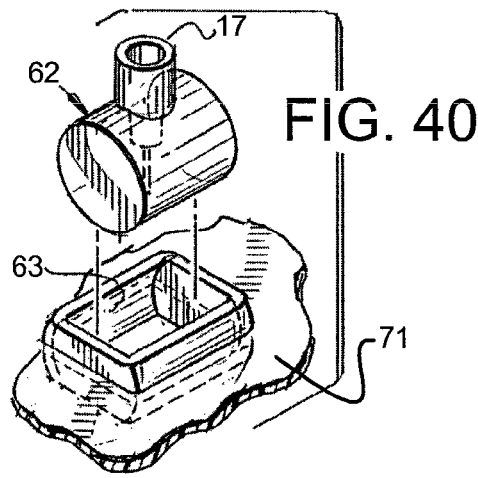
FIG. 40 is an exploded perspective view further illustrating the swivel detail of the embodiment of FIG. 38.

FIG. 38 is a side sectional view of an alternate preferred embodiment of the splash shield device 52 of the present invention, illustrating its operation incorporating an inlet swivel structure permitting better direction of impingement of the saline or other irrigation fluid 57, even for impinging along a wound length direction (as for wound 54) (embodying herein wherein such input opening comprises: a swivel structured and arranged to allow a user to direct a stream of irrigation fluid to selected portions of the skin of a patient; wherein such swivel comprises an attacher structured and arranged to allow attachment of a source of irrigation fluid to such swivel). The details of the inlet swivel structure are best shown in FIGS. 39-40. FIG. 39 is a partial expanded sectional view of the embodiment of FIG. 38, illustrating swivel detail. FIG. 40 is an exploded perspective view further illustrating the swivel detail of the embodiment of FIG. 38. As shown, inlet swivel 62 containing distal opening 17 rides and may rotate in swivel socket 63, which socket is fixed in place by fixed attachment with the distal end wall 71 of splash shield device 52. When the tip 158 of syringe 55 is inserted into distal opening 17, the orifice nozzle 58 of inlet swivel 62 is enabled (see FIG. 39) to direct fluid 56 into the splash shield as shown. The arrangements of FIGS. 32, 33, 34, 35, 36, 37, 38, 39, and 40 embody herein a body structured and arranged to contain irrigation fluid, wherein such body has a maximum height dimension, and an input opening structured and arranged to allow the irrigation fluid into such body, wherein such input opening is located at a substantially lower position than such maximum height dimension; and further embody herein wherein a bottom peripheral circumference of such body has an oval-like shape; and further embody herein wherein such body includes at least one bottom opening; wherein the ratio of a maximum length of such at least one bottom opening compared to a maximum width of such at least one bottom opening is at least 1.5:1.0.

FIG. 41 is a perspective view of yet another preferred embodiment of a splash shield 311 according to the present invention. Splash shield 311 is shown with an inlet port 312 attached to an irrigation syringe 313 and a vacuum connector port 314 attached to a vacuum line 315. FIG. 42 is a side view of the splash shield 311 of FIG. 41, shown attached to the irrigation syringe 313. FIG. 43 is a front view of the splash shield 311 of FIG. 41, with the irrigation syringe 313 in dotted lines. FIG. 44 is a side sectional view of the splash shield 311 of FIG. 41 showing the structural details and fluid flow directions. FIG. 45 is a top view of the splash shield 311 of FIG. 41. FIG. 46 is a partial sectional view through the section 46-46 of FIG. 42. FIG. 47 is a bottom view of the splash shield 311 of FIG. 41.

The illustrated preferred embodiment of splash shield 311 has multiple inlet ports 312 and 312a, with varying internal configurations so that various different kinds of syringes or other fluid containers may be attached and variations in spray fineness may be had. Inlet ports 312 and 312a have male and female connection potential to allow for multiple user preferences with a single manually-operated splash shield 311. Alternately to the inlet port configurations illustrated, such ports may in certain applications protrude into the splash shield 311 or be located within the wall of the splash shield 311. Vacuum connector port 314 is located adjacent base 318 of the splash shield 311 to assist in removal of fluid at the skin surface. As shown, a groove 319 at each bottom side of splash shield 311 acts as a conduit for allowing air and irrigation fluid and debris to be transported to vacuum connector port 314 when downward pressure against the skin is applied while there is a vacuum pull. The grooves 319 form an incomplete seal on a contact surface and widen the base of the splash shield 311, with the groove 319 against the skin becoming an aperture through which such contaminated fluid can be removed. Such groove(s) 319 are preferred to be located near the base of the splash shield 311 to prevent or minimize any visual obstruction caused by the vacuum apparatus features for an observer looking from above (embodying herein an output nozzle structured and arranged to attach to a vacuum line; a conduit structured and arranged to direct suction flow across such splash portion toward such output nozzle; wherein such conduit comprises at least one channel along a periphery of such body extending from such output nozzle to a location approximately at a position symmetrically opposed from the location of such input opening).

The inlet ports 312 and 312a are preferably made to extend in parallel fashion with the vacuum connector port 314 to simplify manufacturing tooling complexity and cost. It is noted that grooves 319 are preferably located adjacent the outer perimeter 321 of the splash shield 311, thus increasing the total surface area of the splash shield 311 without compromising the smaller area that can form an inner protective or operational seal against the skin for wound irrigation protection, particularly for areas of small surface area or sharp contour. For example, over the sharp edge of the chin, one could form an adequate seal with the inner perimeter formed by the inner wall of the groove(s) 319. The lateral outer edges of the grooves would increase the effective surface area protection beyond that formed within the inner seal. This device preferably has a longitudinally tapered base 318 or perimeter 321 to facilitate attachment over the skin; and it preferably has a relief port or contour 325 to facilitate the directional outflow of irrigation effluent or to allow the inflow of gas to facilitate the vacuum of irrigation fluid. It is noted that, if desired for certain uses, the vacuum connector port 314 may be eliminated; and the illustrated device can be operated with or without a vacuum source connected. It is noted that the inlet on the illustrated device is off center, thus providing a design that permits maximum pivoting ability while maintaining efficient shielding. It is also preferred to have flat side edges 318a and 318b of base 318 to maximize stability of the device when pivoted along the edge, as when one is irrigating along a linear laceration.

Figure 48:
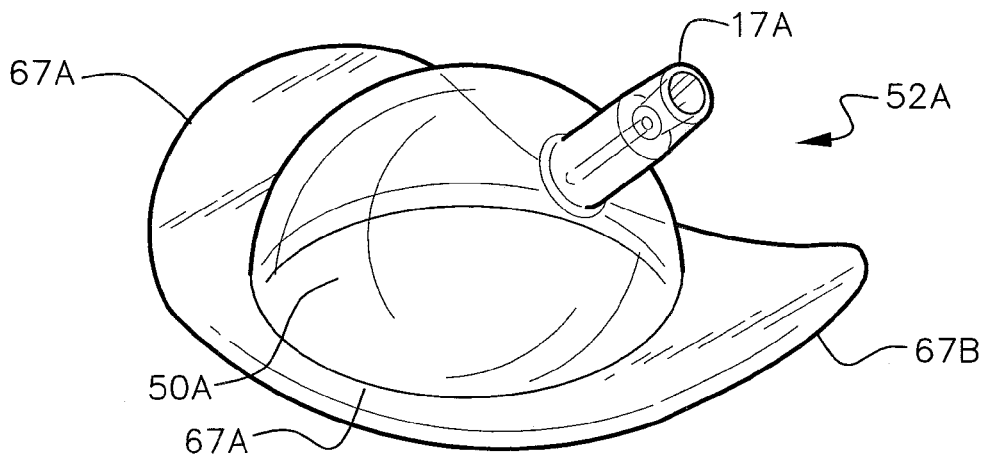
FIG. 48 is a perspective view of another preferred embodiment of a splash shield according to the present invention.
Figure 49:
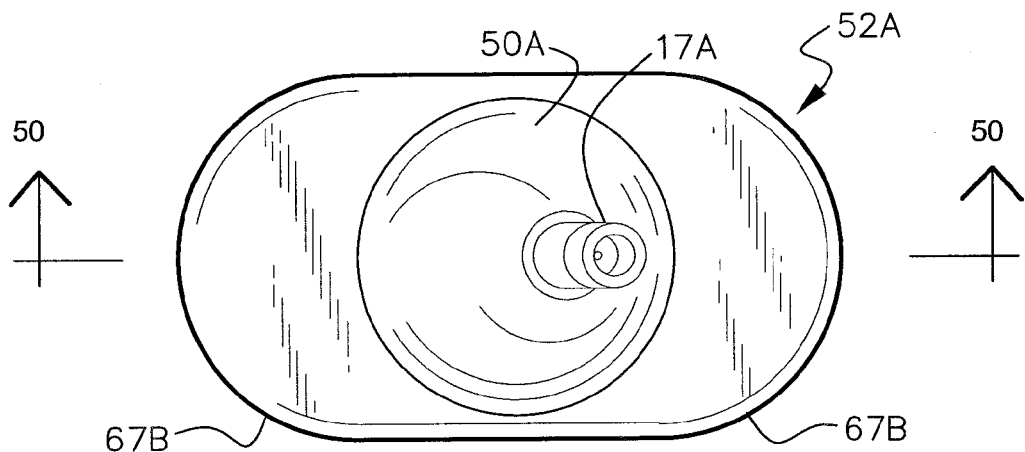
FIG. 49 is a top view of the embodiment of FIG. 48.
Figure 50:
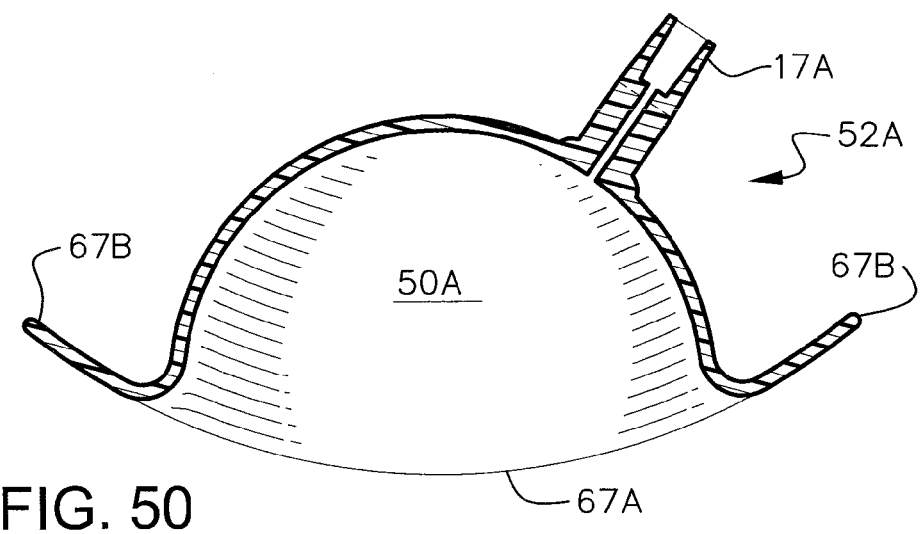
FIG. 50 is a sectional view through the section 50-50 of FIG. 49.

FIGS. 48 (a perspective view), 49 (a top view), and 50 (a sectional view through the section 50-50 of FIG. 49) illustrate another preferred embodiment of a splash shield 52A having many common advantages, arrangements and functions with splash shield device 52, with a few exceptions noted as follows. Bottom portion 67A preferably has a rounded periphery, preferably generally oval or circular, as shown. As shown, extending from this periphery is an extension 67B, as shown, with which to assist rocking of splash shield 52A to better direct the splash stream along the wound and also which performs a function of protecting the fingers and hands of the user from irrigation fluid and wound debris. As shown, bottom portion 67A also implements the "rocker" profile, having a non-planar bottom opening, and non-planar extension 67B. Preferably bottom portion 67A and extension 67B are "saddle-shaped", as shown (embodying herein a transparent body structured and arranged to assist in protecting a user from contact with irrigation fluid directed at a patient's wound; an irrigation-source connector structured and arranged to connect such body, at a first end of such body, to a source of irrigation fluid; wherein such transparent body comprises at least one bottom opening wherein a bottom periphery of such at least one bottom opening is substantially non-planar; and further embodying herein wherein such bottom peripheral circumference is structured and arranged to allow rocking such body; and further embodying herein wherein such bottom peripheral circumference is saddle-shaped).

Further, many other advantages of applicant's invention will be apparent to those skilled in the art from the above descriptions and the below claims.

What is claimed is:

1. A splash shield system, related to protecting at least one user of at least one squeezable wide mouth irrigation fluid bottle from contact with irrigation fluid from at least one squeezable wide mouth irrigation fluid bottle directed at a patient's wound, said splash shield system comprising:

a) at least one body comprising at least one first end and at least one second end; and
b) at least one wide mouth irrigation fluid bottle connector structured and arranged to connect said at least one body, at said at least one first end, to at least one squeezable wide mouth irrigation fluid bottle;
c) wherein said at least one body comprises at least one first inner hollow and at least one second inner hollow; and
d) at least one fluid discharge port;
e) wherein said at least one fluid discharge port is positioned between said at least one first inner hollow and said at least one second inner hollow;
f) wherein said at least one second end is open to said at least one first inner hollow forming at least one shield structured and arranged to protect against contact with irrigation fluid after irrigation fluid has been dispensed from a wide mouth irrigation fluid bottle through said at least one fluid discharge port;
g) wherein said at least one first end is open to said at least one second inner hollow;
h) wherein said squeezable wide mouth irrigation fluid bottle connector comprises threads on the internal surface of said at least one second inner hollow;
i) wherein said at least one first inner hollow has a first volume, said at least one second inner hollow has a second volume, said at least one fluid discharge port has a third volume;
j) wherein said third volume is smaller than said first volume and said second volume; and
k) wherein said at least one shield is transparent to permit viewing of a patient's wound when irrigation fluid is applied to a patient's wound.

2. The splash shield system according to claim 1:
a) wherein said at least one wide mouth irrigation fluid bottle connector is structured and arranged to connect said at least one body, at said at least one first end, to at least one squeezable standard wide mouth irrigation fluid pour bottle;
b) wherein said threads on the internal surface of said at least one second inner hollow are structured and arranged to provide threaded connection with external threads on at least one bottle neck finish of at least one squeezable standard wide mouth irrigation fluid pour bottle;
c) wherein said at least one squeezable standard wide mouth irrigation fluid pour bottle has standard thread dimensions of about a 1½-6 UNC thread dimension; and
d) wherein said at least one squeezable standard wide mouth irrigation fluid pour bottle has standard thread dimensions with a bottle finish inner diameter between about 1.10 inches and 1.25 inches.

3. The splash shield system according to claim 2 wherein:
a) at least one of said at least one first inner hollow and said at least one second inner hollow is capable of temporarily containing at least one volume of irrigation fluid, said at least one volume of irrigation fluid being greater than about 25 milliliters, when said at least one shield is adjacent a body surface of a patient while irrigating a wound; and
b) when said body is connected to a wide mouth irrigation fluid bottle and said wide mouth irrigation fluid bottle is inverted so as to be directed at a patient's wound for irrigation, said at least one shield extends downward toward a patient's wound and below a bottle neck finish portion.

4. The splash shield system according to claim 3 wherein said at least one body consists of a single monolithic piece of plastic.

5. The splash shield system according to claim 3 wherein said at least one fluid discharge port consists of a single circular outlet port.

6. The splash shield system according to 3 wherein said fluid discharge port comprises a total area cross-section, said total area cross-section being at least the cross-sectional area of a single circular port of a 1.5 mm diameter.

7. The splash shield system according to claim 3 wherein:
   a) said at least one fluid discharge port, consists of a single discharge port; and
   b) said at least one squeezable wide mouth irrigation fluid bottle connector and said at least one shield consist of a single monolithic piece of plastic.

8. The splash shield system according to 7 wherein said single discharge port comprises a total area cross-section, said total area cross-section being at least the cross-sectional area of a single circular port of a 1.5 mm diameter.

9. The splash shield system according to claim 3 wherein said at least one fluid discharge port comprises at least two holes structured and arranged to dispense irrigation fluid towards the patient's wound.

10. The splash shield system according to claim 3 wherein said at least one fluid discharge port comprises:
    a) at least two holes structured and arranged to dispense irrigation fluid towards the patient's wound; and
    b) at least one syringe adapter.

11. The splash shield system according to claim 3 wherein:
    a) said at least one fluid discharge port comprises at least two holes structured and arranged to dispense irrigation fluid towards the patient's wound; and
    b) said at least one body consists of a single monolithic piece of plastic.

12. The splash shield system according to claim 3 wherein said at least one body is sterile.

13. The splash shield system according to claim 3 wherein said at least one squeezable wide mouth irrigation fluid bottle connector comprises at least one washer structured and arranged to form a seal when said at least one squeezable wide mouth irrigation fluid bottle connector is connected to at least one squeezable wide mouth irrigation fluid bottle.

14. The splash shield system according to claim 3 wherein:
    a) said at least one squeezable wide mouth irrigation fluid bottle connector comprises at least one ridge structured and arranged to form a seal when said at least one squeezable wide mouth irrigation fluid bottle connector is connected to at least one squeezable wide mouth irrigation fluid bottle; and
    b) said at least one ridge protrudes within said at least one second hollow.

15. The splash shield system according to claim 3 wherein said splash shield system further comprises:
    a) at least one nozzle comprising
       i) at least one inlet port,
       ii) at least one passageway, and
       iii) at least one outlet port;
    b) wherein said at least one passageway comprises at least one cross-sectional area; and
    c) wherein said at least one cross-sectional area decreases from said at least one inlet port of said at least one nozzle to said at least one outlet port of said at least one nozzle.

16. The splash shield system according to claim 3 wherein said at least one wide mouth irrigation fluid bottle connector is structured and arranged to connect to multiple bottle finish types.

17. The splash shield system according to claim 3 further comprising:
    a) at least one partition between said at least one first end and said at least one second end;
    b) wherein said at least one partition further comprises at least one nozzle protruding from said at least one partition into said at least one shield; and
    c) wherein said body consists of a single monolithic piece of plastic.

18. The splash shield system according to claim 3 wherein said at least one body comprises at least one substantially cylindrical wall portion.

19. The splash shield system according to claim 3 wherein said at least one shield is substantially round.

20. The splash shield system according to claim 2 comprising at least one hollow discharge port extension.

21. The splash shield system according to claim 20 wherein said at least one hollow discharge port extension extends beyond at least one of said first and second ends of said body.

22. The splash shield system according to claim 20 wherein said at least one hollow discharge port extension extends beyond an outer edge of said at least one first inner hollow.

23. The splash shield system according to claim 1 wherein said at least one wide mouth irrigation fluid bottle connector is structured and arranged to connect to multiple bottle finish types.

24. The splash shield system according to claim 23 wherein said at least one squeezable wide mouth irrigation fluid bottle connector comprises at least one washer structured and arranged to form a seal with multiple bottle finish types.

25. The splash shield system according to claim 23 wherein
    a) said at least one squeezable wide mouth irrigation fluid bottle connector comprises at least one ridge protruding within said at least one second hollow; and
    b) said ridge and said at least one squeezable wide mouth irrigation fluid bottle connector consist of a single monolithic piece of plastic.

26. The splash shield system according to claim 1 further comprising:
    a) at least one partition between said at least one first end and said at least one second end; and said at least one partition further comprises said at least one fluid discharge port protruding from said at least one partition.

27. The splash shield system according to claim 26 further comprising at least one nozzle, protruding from said at least one partition into said at least one shield.

28. The splash shield system according to claim 27 comprising at least one hollow discharge port extension.

29. The splash shield system according to claim 28 wherein said at least one hollow discharge port extension extends beyond at least one end of said body.

30. The splash shield system according to claim 28 wherein said at least one hollow discharge port extension extends beyond an outer edge of said at least one first inner hollow.

31. The splash shield system according to claim 26 further comprising:
    a) at least one nozzle, protruding from said at least one partition into said at least one shield;
    b) wherein said body consists of a single monolithic piece of plastic.

32. The splash shield system according to claim 26 further comprising at least one tubing extending beyond an outer edge of said shield.

33. The splash shield system according to claim 1 wherein said at least one squeezable wide mouth irrigation fluid bottle connector comprises at least one washer structured and arranged to form a seal when said at least one squeezable wide mouth irrigation fluid bottle connector is connected to the at least one squeezable wide mouth irrigation fluid bottle.

34. The splash shield system according to claim 33 wherein said at least one washer comprises a circular ridge protruding within said at least one second hollow.

35. The splash shield system according to claim 1 wherein said at least one shield extends beyond the rim of a wide mouth irrigation fluid bottle when connected to a wide mouth irrigation fluid bottle.

36. The splash shield system according to claim 1 wherein, when connected to a wide mouth irrigation fluid bottle and inverted so as to be directed at a patient's wound for irrigation, said at least one shield extends downward toward a patient's wound and below the rim of a wide mouth irrigation fluid bottle.

37. The splash shield system according to claim 1 comprising at least one hollow discharge port extension.

38. The splash shield system according to claim 37 wherein said at least one hollow discharge port extension extends beyond at least one end of said body.

39. The splash shield system according to claim 37 wherein said at least one hollow discharge port extension extends beyond an outer edge of said at least one first inner hollow.

40. The splash shield system according to claim 39 wherein said at least one hollow discharge port extension is flexible.

41. The splash shield system according to claim 39 wherein said at least one hollow discharge port extension is a flexible tube with a substantially uniform inner diameter and a substantially uniform outer diameter along at least most of the length of the flexible tube.

42. The splash shield system according to claim 1 wherein said at least one fluid discharge port consists of a single discharge port structured and arranged to dispense a single concentrated discharge stream.

43. The splash shield system according to claim 1 wherein said at least one fluid discharge port comprises at least two holes structured and arranged to dispense irrigation fluid towards a patient's wound.

44. The splash shield system according to claim 1 wherein said at least one body is sterile.

45. The splash shield system according to claim 1 further comprising at least one syringe connector in fluid communication with said at least one fluid discharge port.

46. The splash shield system according to claim 1 further comprising at least one squeezable wide mouth irrigation fluid bottle.

47. The splash shield system according to claim 1 further comprising at least one squeezable standard wide mouth irrigation fluid pour bottle.

48. The splash shield system according to claim 1 wherein:
a) said at least one wide mouth irrigation fluid bottle connector is structured and arranged to connect to at least one squeezable wide mouth irrigation fluid bottle neck finish portion comprising at least one outer diameter between about ⅘ inches and about 1¾ inches;
b) said at least one squeezable wide mouth irrigation fluid bottle connector is structured and arranged to connect to at least one squeezable wide mouth irrigation fluid bottle having a volume between about 250 cubic centimeters and about 1750 cubic centimeters;
c) said at least one squeezable wide mouth irrigation fluid bottle connector comprises at least one inner diameter between about ⅘ inches and about 1¾ inches;
d) at least one of said first and second inner hollows is capable of temporarily containing at least one volume of irrigation fluid, said at least one volume of irrigation fluid being greater than about 25 milliliters, when said at least one shield is adjacent a body surface of a patient while irrigating a wound; and
e) when said body is connected to a squeezable wide mouth irrigation fluid bottle and said wide mouth irrigation fluid bottle is inverted so as to be directed at a patient's wound for irrigation, said at least one shield extends downward toward a patient's wound and below the bottle neck finish portion.

49. The splash shield system according to claim 48 wherein said at least one fluid discharge port comprises at least two holes structured and arranged to dispense irrigation fluid towards the patient's wound.

50. The splash shield system according to claim 49 further comprising at least one nozzle comprising:
a) at least one inlet port;
b) at least one passageway; and
c) at least one outlet port;
d) wherein said at least one body consists of a single piece of plastic;
e) wherein said at least one passageway comprises at least one cross-sectional area;
f) wherein said at least one cross-sectional area decreases from said at least one inlet port of said at least one nozzle to said at least one outlet port of said at least one nozzle; and
g) wherein said at least one shield is substantially round and comprises at least one side port structured and arranged to permit evacuation of irrigation fluid temporarily contained by said at least one inner hollow.

51. The splash shield system according to claim 50 comprising at least one squeezable irrigation fluid bottle;
a) wherein said at least one body comprises at least one circular ridge protruding within said at least one second inner hollow structured and arranged to form a seal with an irrigation bottle;
b) wherein said at least one body is sterile;
c) wherein said at least one wide mouth irrigation fluid bottle connector is structured and arranged to connect to multiple bottle finish types; and
d) wherein said at least one shield comprises a substantially round and cylindrical wall portion.

52. The splash shield system according to claim 48 wherein said at least one body consists of a single monolithic piece of plastic.

53. The splash shield system according to claim 48 wherein said at least one fluid discharge port consists of a single circular outlet port.

54. The splash shield system according to claim 48 wherein said at least one fluid discharge port, consists of a single discharge port having a total cross-sectional area that is at least the cross-sectional area of a single circular port of a 1.5 mm diameter.

55. The splash shield system according to claim 48 wherein:
a) said at least one fluid discharge port, consists of a single discharge port having a total cross-sectional area that is at least the cross-sectional area of a single circular port of a 1.5 mm diameter; and
b) said at least one body consists of a single monolithic piece of plastic.

56. The splash shield system according to claim 48 wherein said at least one body comprises at least one substantially cylindrical wall portion.

57. The splash shield system according to claim 48 wherein said at least one shield is substantially round.

58. The splash shield system according to claim 48 wherein said at least one shield comprises a substantially round and cylindrical wall portion.

59. The splash shield system according to claim 1 comprises at least one side port structured and arranged to permit evacuation of irrigation fluid temporarily contained by said at least one inner hollow.

60. A splash shield system, related to protecting at least one user of at least one irrigation fluid device from contact with irrigation fluid from at least one irrigation fluid device directed at a patient's wound, said splash shield system comprising:
   a) at least one body comprising at least one first end and at least one second end;
   b) at least one luer connector structured and arranged to connect said at least one body to at least one irrigation fluid device;
   c) wherein said at least one body comprises at least one first inner hollow;
   d) at least one fluid discharge port having a proximal end and a distal end,
   e) at least one hollow fluid discharge port extension having at least one proximal end and at least one distal end, said proximal end of said at least one hollow fluid discharge port extension attached to said body between said at least one first end and said at least one second end of said at least one body;
   f) wherein said at least one second end is open to said at least one first inner hollow forming at least one shield structured and arranged to protect against contact with irrigation fluid after irrigation fluid has been dispensed through said at least one fluid discharge port directed at a patient's wound;
   g) wherein said at least one shield is transparent to permit viewing of a patient's wound when irrigation fluid is applied to a patient's wound;
   h) wherein said at least one first inner hollow has at least one first volume, said at least one luer connector has at least one second volume, and said at least one hollow fluid discharge port has at least one third volume;
   i) wherein said at least one third volume is smaller than said at least one first volume;
   j) wherein said at least one distal end of said at least one hollow fluid discharge port extension is positioned beyond said at least one first hollow;
   k) wherein said at least one luer connector and said at least one shield are monolithic.

61. The splash shield system according to claim 60 wherein said at least one hollow fluid discharge port extension comprises at least one elongated nozzle.

62. The splash shield system according to claim 61 wherein said tip of said at least one elongated nozzle end terminates within said at least one first inner hollow.

63. The splash shield system according to claim 61 wherein said at least one luer connector, said at least one shield, and said elongated nozzle are monolithic.

64. The splash shield system according to claim 60 wherein said at least one hollow fluid discharge port extension is removable from said at least one body.

65. The splash shield system according to claim 60 wherein said at least one distal end of said at least one hollow fluid discharge port extension is flexible.

66. The splash shield system according to claim 60 wherein said at least one hollow fluid discharge port extension comprises at least one tube with a substantially uniform inner diameter and a substantially uniform outer diameter along at least most of the length of said at least one tube.

67. The splash shield system according to claim 66 wherein said at least one tube is flexible.

68. The splash shield system according to claim 60 further comprising at least one wide mouth irrigation fluid bottle connector, having threads structured and arranged to connect said at least one body, at said at least one first end, to at least one squeezable wide mouth irrigation fluid bottle.

69. The splash shield system according to claim 60 further comprising at least one squeezable irrigation bottle connector structured and arranged to connect said at least one body, at said at least one first end, to at least one squeezable irrigation fluid bottle.

\* \* \* \* \*